(12) United States Patent
Buck et al.

(10) Patent No.: US 10,410,768 B2
(45) Date of Patent: Sep. 10, 2019

(54) PROBE ASSEMBLY HAVING CABLE ASSEMBLY WITH WIRE PAIRS

(71) Applicant: TE CONNECTIVITY CORPORATION, Berwyn, PA (US)

(72) Inventors: Arthur G. Buck, Sherwood, OR (US); Paul C. Sprunger, Dundee, OR (US); Kevin T. Lewis, Portland, OR (US); Yevgeniy Mayevskiy, Newberg, OR (US); Thomas J. Medina, Portland, OR (US); Thuong A. Huynh, Beaverton, OR (US)

(73) Assignee: GREGANNA UNLIMITED COMPANY, Galway (IE)

( * ) Notice: Subject to any disclaimer, the term of this patent is extended or adjusted under 35 U.S.C. 154(b) by 0 days.

(21) Appl. No.: 15/796,742

(22) Filed: Oct. 27, 2017

(65) Prior Publication Data

US 2018/0247741 A1 Aug. 30, 2018

Related U.S. Application Data

(60) Provisional application No. 62/464,676, filed on Feb. 28, 2017.

(51) Int. Cl.
*H01B 11/02* (2006.01)
*H01B 7/02* (2006.01)
(Continued)

(52) U.S. Cl.
CPC ............... *H01B 11/02* (2013.01); *A61B 8/44* (2013.01); *A61B 8/56* (2013.01); *H01B 7/02* (2013.01);
(Continued)

(58) Field of Classification Search
CPC combination set(s) only.
See application file for complete search history.

(56) References Cited

U.S. PATENT DOCUMENTS 1,726,551 A * 9/1929 Stearns .................. H01B 11/04
174/34
4,381,426 A 4/1983 Cronkite et al.
(Continued)

FOREIGN PATENT DOCUMENTS

EP 0061246 A1 9/1982

OTHER PUBLICATIONS

International Search Report dated May 15, 2018, for corresponding International Application No. PCT/US2018/020028.

*Primary Examiner* — William H. Mayo, III
*Assistant Examiner* — Krystal Robinson

(57) ABSTRACT

Probe assembly includes an ultrasound probe and a cable assembly configured to communicatively couple the ultrasound probe to a control system and transmit signals therethrough. The cable assembly includes a cable jacket surrounding a channel of the cable assembly. The cable assembly also includes a plurality of wire pairs extending through the channel. The channel being sized and shaped to permit the wire pairs to move relative to one another within the channel when the probe assembly is moved. The wire pairs and the channel are configured to have a designated pack ratio (Area$^{WPS}$/Area$^C$). The Area$^{WPS}$ includes a collective cross-sectional area of the wire pairs, and the Area$^C$ is equal to a cross-sectional area of the channel.

18 Claims, 11 Drawing Sheets

(51) Int. Cl.
*A61B 8/00* (2006.01)
*B06B 1/02* (2006.01)
*B06B 1/06* (2006.01)
*H01B 7/08* (2006.01)

(52) U.S. Cl.
CPC .......... *A61B 8/4444* (2013.01); *B06B 1/0292* (2013.01); *B06B 1/0622* (2013.01); *H01B 7/0892* (2013.01)

(56) References Cited

U.S. PATENT DOCUMENTS

| | | | |
|---|---|---|---|
| 4,767,891 A | 8/1988 | Biegon et al. | |
| 6,314,182 B1 * | 11/2001 | Brandt | H01R 9/035 333/185 |
| 6,580,034 B2 * | 6/2003 | Daane | H01B 7/0892 174/113 R |
| 7,999,184 B2 * | 8/2011 | Wiebelhaus | H01B 11/002 174/113 C |
| 2003/0111255 A1 | 6/2003 | Buck et al. | |

\* cited by examiner

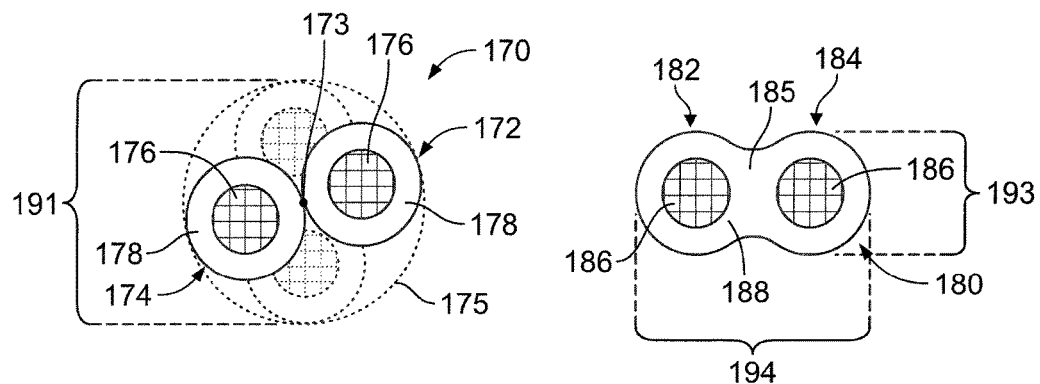
FIG. 3A  FIG. 3B
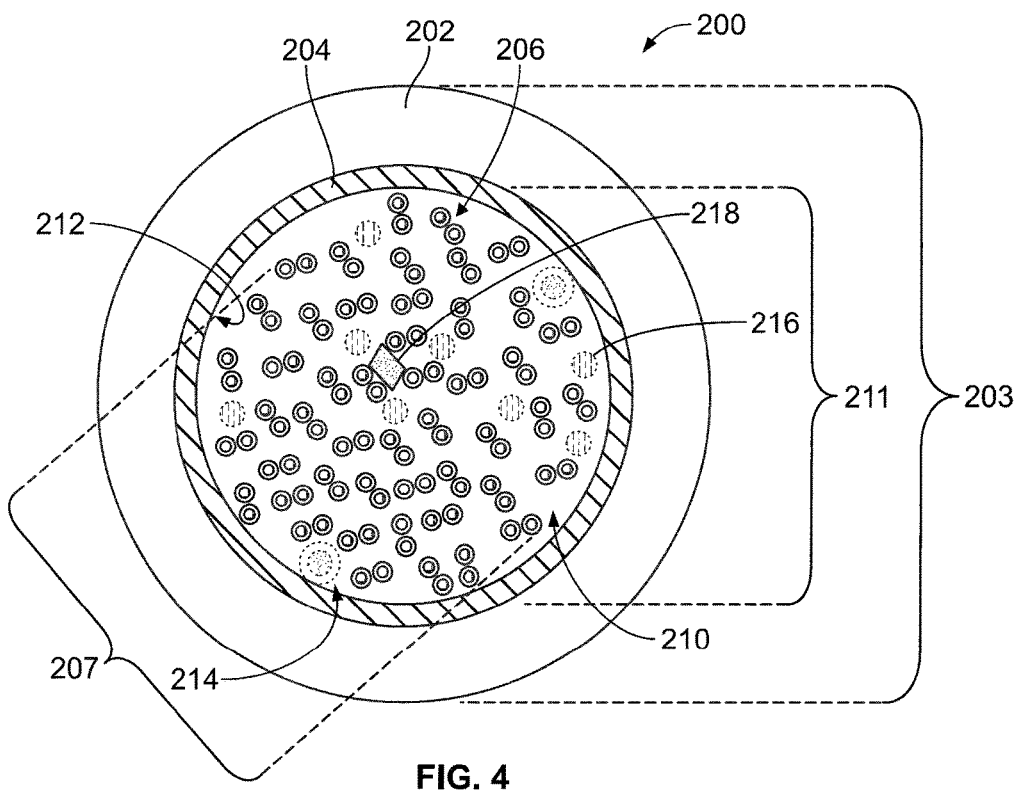
FIG. 4

PROBE ASSEMBLY HAVING CABLE ASSEMBLY WITH WIRE PAIRS

CROSS-REFERENCE TO RELATED APPLICATIONS

The present application claims the benefit of U.S. Provisional Application No. 62/464,676, filed on February 28, which is incorporated herein by reference in its entirety.

BACKGROUND

The subject matter set forth herein relates generally to cable assemblies and probe assemblies that use wires to communicate signals to and/or from a device.

The medical industry may use cable assemblies to communicate data to and/or from a probe or other medical device. There is a general market demand to reduce at least one of the size, weight, and/or cost of the cable assemblies. It is also often desirable to improve the ergonomics of the medical device or assembly so that the medical device is easier to handle. For example, an ultrasound probe assembly uses a cable assembly to interconnect an ultrasound device (or the ultrasound probe) to a control system or device. High-end medical ultrasound imaging utilizes tens and hundreds of piezo-electric transducer elements to achieve a quality image that can be helpful for diagnosing a condition of the patient and/or assessing the condition of the patient. The transducer elements require individual pathways or conductors to the control system. Conventional ultrasound probe assemblies may bundle the conductors in a concentric configuration with the conductors being wrapped around one axis of the cable assembly.

If the cables are heavy and/or inflexible, the operator may experience an excessive amount of strain on the wrist, forearm, or elbow. In order to maintain a practical size of the cable assembly and not to impose excessive stress on the sonographer, the conductors are small coaxial conductors, which may be referred to as micro-coaxial conductors. Examples of such micro-coaxial conductors include 42 AWG coaxial conductors or smaller. The micro-coaxial conductors transmit signals between the probe and the control system.

It can be challenging, however, to fit multiple signal lines, such as 256 separate micro-coaxial conductors, into a cable assembly while keeping the cable assembly small enough so that the cable assembly is practical. It can also be costly to produce the micro-coaxial conductors (or the cable assemblies that include such conductors) because of the multiple processes involved.

BRIEF DESCRIPTION

In an embodiment, an assembly (e.g., probe assembly) is provided that includes a modular device (e.g., ultrasound probe) and a cable assembly configured to communicatively couple the modular device to a control system and transmit analog signals therethrough. The cable assembly includes a cable jacket surrounding a channel of the cable assembly. The cable assembly also includes at least 32 wire pairs extending through the channel. The channel is sized and shaped to permit the wire pairs to move relative to one another within the channel when the assembly is moved. The channel is an available space through which the wire pairs and other longitudinal elements, if any, are permitted to extend through during operation of the assembly. The wire pairs and the channel are configured to have a designated pack ratio ($Area^{WPS}/Area^C$). The $Area^{WPS}$ includes a collective cross-sectional area of the wire pairs and the longitudinal elements, if any, extending through the channel. The $Area^C$ is equal to a cross-sectional area of the channel. The designated pack ratio being between 0.20 and 0.75.

In some aspects, the wire pairs include first twisted pairs and second twisted pairs. Each of the first twisted pairs is twisted in a first direction about a central axis of the corresponding first twisted pair. Each of the second twisted pairs is twisted in an opposite second direction about a central axis of the corresponding second twisted pair.

Optionally, the first twisted pairs and the second twisted pairs are interspersed within the channel.

Optionally, the twisted pairs form a plurality of ribbon layers in which each of the ribbon layers has at least two of the first twisted pairs and at least two of the second twisted pairs. Optionally, the first twisted pairs and the second twisted pairs have an alternating arrangement with respect to one another for each ribbon layer, wherein the alternating arrangement includes at least one of: (a) each first twisted pair being adjacent to at least one second twisted pair or (b) each second twisted pair being adjacent to at least one first twisted pair.

In some aspects, the probe assembly also includes a communication sub-assembly having a printed circuit. The first and second twisted pairs are terminated to the printed circuit.

In an embodiment, a probe assembly is provided that includes an ultrasound device and a cable assembly configured to communicatively couple the ultrasound device to a control system and transmit signals, such as analog signals, there through. The cable assembly includes a cable jacket surrounding a channel of the cable assembly. The cable assembly also includes a plurality of wire pairs extending through the channel that each include an insulated signal wire and an insulated ground wire. The channel includes a channel that is occupied, at least in part, by the wire pairs. In some embodiments, the channel includes empty space between the wire pairs such that the wire pairs are permitted to move relative to one another within the empty space when the probe assembly is moved. The empty space may be occupied by, for example, ambient air or a predetermine gas (e.g., argon gas). The wire pairs and the channel are configured to have a designated pack ratio ($Area^{WPS}/Area^C$). The $Area^{WPS}$ includes a collective cross-sectional area of the wire pairs and other solid material (e.g., longitudinal elements), if any, extending through the channel. The channel is a space through which the wire pairs and the longitudinal elements, if any, are permitted to extend through during operation of the probe assembly. The $Area^C$ is equal to a cross-sectional area of the channel. The designated pack ratio being between 0.20 and 0.75.

In some aspects, the channel is occupied by the wire pairs and, at least, a filler liquid. The filler liquid may be, for example, a viscous liquid (e.g., silicone gel) or a less viscous liquid. The viscosity of the liquid may permit some movement of the wire pairs relative to one another. The filler liquid is essentially incompressible, thereby permitting the wire pairs to move. The filler liquid does not form part of the $Area^{WPS}$. The space in which the filler liquid is disposed may be part of the $Area^C$. Accordingly, the channel may be occupied by one or more gases, liquids, or gels that permit free movement of the wire pairs therein. The gases, liquids, or gels may be selected to permit a designated range of movement and/or achieve a designated performance for the cable assembly.

In some aspects, the designated pack ratio is between 0.45 and 0.65.

In some aspects, the cable assembly also includes longitudinal elements that extend within the channel. The Area$^{WPS}$ includes the collective cross-sectional area of the wire pairs and the collective cross-sectional area of the longitudinal elements. The longitudinal elements may include, for example, other types of electrical conductors, optical fibers, or non-conductive (e.g., plastic) spacers that separate the wire pairs.

In some aspects, the wire pairs include twisted pairs. The Area$^{WPS}$ includes the collective cross-sectional area of the wire pairs, which includes the full area taken up by the twist of each pair.

In some aspects, the insulated ground wire includes a wire conductor having a first cross-sectional area and the insulated signal wire includes a wire conductor having a second cross-sectional area. The first cross-sectional area is greater than the second cross-sectional area. Optionally, these wire pairs include twisted pairs. Optionally, the insulated ground wire and the insulated signal wire have equal cross-sectional dimensions (e.g., equal diameters). In other embodiments, the insulated signal wire may have a cross-sectional dimension that is greater than the cross-sectional dimension of the insulated ground wire.

In some aspects, the wire pairs include first twisted pairs and second twisted pairs. The first twisted pairs are twisted in a first direction. The second twisted pairs are twisted in an opposite second direction.

Optionally, the first twisted pairs and the second twisted pairs are interspersed within the channel. For example, each first twisted pair may be adjacent to at least one second twisted pair and each second twisted pair may be adjacent to at least one first twisted pair at a mid-point along the length of the cable jacket.

Optionally, the first and second twisted pairs have essentially fixed positions with respect to each other proximate to the ultrasound device and/or proximate to an end of the cable jacket. The first twisted pairs and the second twisted pairs have an alternating arrangement with respect to one another. In some embodiments, the alternating arrangement includes the first twisted pairs and the second twisted pairs being substantially evenly distributed with respect to one another. In some embodiments, the alternating arrangement includes at least one of: (a) each first twisted pair being adjacent to at least one second twisted pair or (b) each second twisted pair being adjacent to at least one first twisted pair.

In some aspects, the probe assembly is configured to communicate analog signals through the wire pairs at frequencies between 0.5 MHz and 50.0 MHz. In other aspects, however, the probe assembly is configured to communicate digital signals through the wire pairs.

In some aspects, maximum near end crosstalk of the probe assembly is −26 dB or better (e.g., lower).

In an embodiment, a probe assembly is provided that includes an ultrasound device and a cable assembly configured to communicatively couple the ultrasound device to a control system and transmit signals therethrough. The cable assembly includes a cable jacket surrounding a channel of the cable assembly and a plurality of wire pairs extending through the channel that each include an insulated signal wire and an insulated ground wire. The wire pairs are packed within the channel such that the wire pairs have essentially fixed relative positions at designated cross-sections. The wire pairs have a braided configuration in which the wire pairs are interweaved in a designated manner such that near end crosstalk does not exceed a target amount during operation of the probe assembly.

In some aspects, the target amount of the near end crosstalk is at most −26 dB. Optionally, the probe assembly is configured to communicate analog signals through the wire pairs at frequencies between 0.5 MHz and 50.0 MHz. Optionally, the probe assembly may be configured to communicate digital signals.

In some aspects, the cable assembly includes at least 16 wire pairs.

In some aspects, the designated cross-sections include first, second, and third cross-sections that are at least ten centimeters apart along a length of the cable assembly. The wire pairs at each of the first, second, and third cross-sections having a cross-sectional arrangement. The cross-sectional arrangements of the first, second, and third cross-sections are different.

In some aspects, the wire pairs include twisted pairs.

In some aspects, the insulated ground wire has a first cross-sectional area and the insulated signal wire has a second cross-sectional area. The first cross-sectional area is greater than the second cross-sectional area. Optionally, the wire pairs include twisted pairs.

In some aspects, the wire pairs include first twisted pairs and second twisted pairs. The first twisted pairs are twisted in a first direction, and the second twisted pairs are twisted in an opposite second direction.

In some aspects, the first twisted pairs and the second twisted pairs are interspersed within the channel. For example, each first twisted pair may be adjacent to at least one second twisted pair and each second twisted pair may be adjacent to at least one first twisted pair.

In some aspects, a probe assembly is provided that includes an ultrasound device and a cable assembly configured to communicatively couple the ultrasound device to a control system and transmit signals therethrough. The cable assembly includes a cable jacket surrounding a channel of the cable assembly and a plurality of twisted pairs extending through the channel that each include an insulated signal wire and an insulated ground wire. The twisted pairs include first twisted pairs and second twisted pairs. The first twisted pairs are twisted in a first direction. The second twisted pairs are twisted in an opposite second direction.

In some aspects, the first twisted pairs and the second twisted pairs are interspersed within the channel. For example, each first twisted pair may be adjacent to at least one second twisted pair and each second twisted pair may be adjacent to at least one first twisted pair.

In some aspects, the first and second twisted pairs have essentially fixed positions with respect to each other at a designated location along the cable assembly. The first twisted pairs and the second twisted pairs have an alternating arrangement with respect to one another at the designated location. Optionally, the alternating arrangement includes the first twisted pairs and the second twisted pairs being substantially evenly distributed with respect to one another. Optionally, the alternating arrangement includes at least one of: (a) each first twisted pair being adjacent to at least one second twisted pair or (b) each second twisted pair being adjacent to at least one first twisted pair.

In some aspects, the insulated ground wire has a first cross-sectional area and the insulated signal wire has a second cross-sectional area. The first cross-sectional area may be greater than the second cross-sectional area.

The channel may include an empty space that is occupied by one or more gases, including ambient air or a predetermined gas (e.g., argon). The channel may also include a filler liquid that exists between the wire pairs. The filler liquid may be, for example, a liquid having an essentially constant volume. The gases or the filler liquid permit the wire pairs to move relative to one another within the channel when the probe assembly is moved. The wire pairs and the channel are configured to have a designated pack ratio ($Area^{WPS}/Area^C$), wherein the $Area^{WPS}$ includes a collective cross-sectional area of the wire pairs and other longitudinal elements, if any, and the $Area^C$ is equal to a cross-sectional area of the channel. The $Area^{WPS}$ does not include gases, liquids, or gels that permit movement of the wire pairs. The designated pack ratio may be, for example, between 0.20 and 0.75.

In an embodiment, a probe assembly is provided that includes an ultrasound device and a cable assembly configured to communicatively couple the ultrasound device to a control system and transmit signals therethrough. The cable assembly includes a cable jacket surrounding a channel of the cable assembly and a plurality of twisted pairs extending through the channel that each include an insulated signal wire and an insulated ground wire. The insulated ground wire has a first cross-sectional area and the insulated signal wire has a second cross-sectional area. The first cross-sectional area is greater than the second cross-sectional area.

In some aspects, the insulated ground wire includes a ground conductor and the insulated signal wire includes a signal conductor. The ground conductor has a greater cross-sectional area than a cross-sectional area of the signal conductor.

In some aspects, an insulation of the insulated ground wire has a smaller thickness than an insulation of the insulated signal wire.

In some aspects, the twisted pairs include first twisted pairs and second twisted pairs. The first twisted pairs are twisted in a first direction, and the second twisted pairs are twisted in an opposite second direction.

Optionally, the first twisted pairs and the second twisted pairs are interspersed within the channel. For example, each first twisted pair may be adjacent to at least one second twisted pair and each second twisted pair may be adjacent to at least one first twisted pair.

Optionally, the first and second twisted pairs have essentially fixed positions with respect to each other at a designated location along the cable assembly. The first twisted pairs and the second twisted pairs have an alternating arrangement with respect to one another at the designated location. In some embodiments, the alternating arrangement includes the first twisted pairs and the second twisted pairs being substantially evenly distributed with respect to one another. In some embodiments, the alternating arrangement includes at least one of: (a) each first twisted pair being adjacent to at least one second twisted pair or (b) each second twisted pair being adjacent to at least one first twisted pair.

In some aspects, the channel is sized and shaped to include a substantial amount of space existing between the wire pairs and other optional longitudinal elements (e.g., other wires or spacers). The space may be an empty space or void. For example, the empty space or void may include one or more gases having a known or unknown composition. More specifically, the empty space may include ambient air or a predetermined gas. The gas or gases permit the twisted pairs to move relative to one another within the empty space when the probe assembly is moved. The twisted pairs and the channel are configured to have a designated pack ratio ($Area^{WPS}/Area^C$), wherein the $Area^{WPS}$ includes a collective cross-sectional area of the twisted pairs and the longitudinal elements, if any, and the $Area^C$ is equal to a cross-sectional area of the channel. The designated pack ratio may be between 0.20 and 0.70.

In other aspects, the channel incudes a filler liquid, such as an aqueous-like liquid or a gel (e.g., silicone gel). The filler liquid may also permit the twisted pairs to move relative to one another. The filler liquid, however, may impede movement of the twisted pairs more so than empty space.

In an embodiment, a cable assembly is provided that includes a cable jacket surrounding a channel of the cable assembly. The cable jacket extends between opposite ends. At least 32 wire pairs extend through the channel. The channel is sized and shaped to permit the wire pairs to move relative to one another within the channel when the probe assembly is moved. The channel is an available space through which the wire pairs and other longitudinal elements, if any, are permitted to extend through the cable jacket during usage of the cable assembly. The wire pairs and the channel are configured to have a designated pack ratio ($Area^{WPS}/Area^C$), wherein the $Area^{WPS}$ includes a collective cross-sectional area of the wire pairs and the longitudinal elements, if any, extending through the channel. The $Area^C$ is equal to a cross-sectional area of the channel. The designated pack ratio being between 0.20 and 0.75.

In some aspects, the wire pairs include first twisted pairs and second twisted pairs. Each of the first twisted pairs is twisted in a first direction about a central axis of the corresponding first twisted pair, and each of the second twisted pairs is twisted in an opposite second direction about a central axis of the corresponding second twisted pair. Optionally, the first twisted pairs and the second twisted pairs are interspersed within the channel.

In some aspects, wherein the designated pack ratio is between 0.45 and 0.65.

In some aspects, each of the wire pairs includes an insulated ground wire having a wire conductor and an insulation layer and also includes an insulted signal wire having a wire conductor and an insulation layer. The wire conductor of the insulated ground wire has a first cross-sectional area, and the wire conductor of the insulated signal wire has a second cross-sectional area. The first cross-sectional area is greater than the second cross-sectional area.

In some aspects, the cable assembly also includes a communication sub-assembly having a printed circuit. The wire pairs are terminated to the printed circuit.

In an embodiment, a cable assembly is provided that includes a cable jacket surrounding a channel of the cable assembly. The cable jacket extends between opposite ends. The cable assembly also includes a plurality of wire pairs extending through the channel that each include an insulated signal wire and an insulated ground wire. The channel, as described herein, is sized and shaped so that the wire pairs are permitted to move relative to one another within the channel when the probe assembly is moved. The wire pairs and the channel are configured to have a designated pack ratio ($Area^{WPS}/Area^C$). The $Area^{WPS}$ includes a collective cross-sectional area of the wire pairs and other longitudinal elements, if any, and the $Area^C$ is equal to a cross-sectional area of the channel. The designated pack ratio is between 0.20 and 0.75. End segments or portions of the wire pairs may be coupled in designated groups, which may be positioned within the channel, at each end of the cable jacket, or at a point after clearing the cable jacket.

In an embodiment, a cable assembly is provided. The cable assembly includes a cable jacket surrounding a channel of the cable assembly. The cable jacket extends between opposite ends. The cable assembly also includes at least 32 twisted pairs extending through the channel that each include an insulated signal wire and an insulated ground wire. The twisted pairs include first twisted pairs and second twisted pairs. The first twisted pairs are twisted in a first direction, and the second twisted pairs are twisted in an opposite second direction.

In an embodiment, a cable assembly is provided that includes a cable jacket surrounding a channel of the cable assembly. The cable jacket extends between opposite ends. The cable assembly also includes a plurality of twisted pairs extending through the channel that each include an insulated signal wire and an insulated ground wire. The twisted pairs include first twisted pairs and second twisted pairs. The first twisted pairs are twisted in a first direction, and the second twisted pairs being twisted in an opposite second direction. End segments or portions of the wire pairs may be coupled in designated groups, which may be positioned within the channel, at each end of the cable jacket, or at a point after clearing the cable jacket.

In one or more of the above embodiments, the probe assembly may be configured to communicate analog signals through the wire pairs at frequencies between 0.5 MHz and 50.0 MHz, although probe assemblies configured to communicate digital signals are also contemplated.

In one or more of the above embodiments, a maximum near end crosstalk of the probe assembly may be −26 dB or better.

BRIEF DESCRIPTION OF THE DRAWINGS

FIG. 3A illustrates a cross-section of a twisted pair that may be used with the cable assembly of FIG. 2.

FIG. 3B illustrates a cross-section of a parallel pair that may be used with the cable assembly of FIG. 2.

FIG. 4 is a cross-section of a cable assembly having a designated pack ratio formed in accordance with an embodiment.

DETAILED DESCRIPTION

Figure 1:
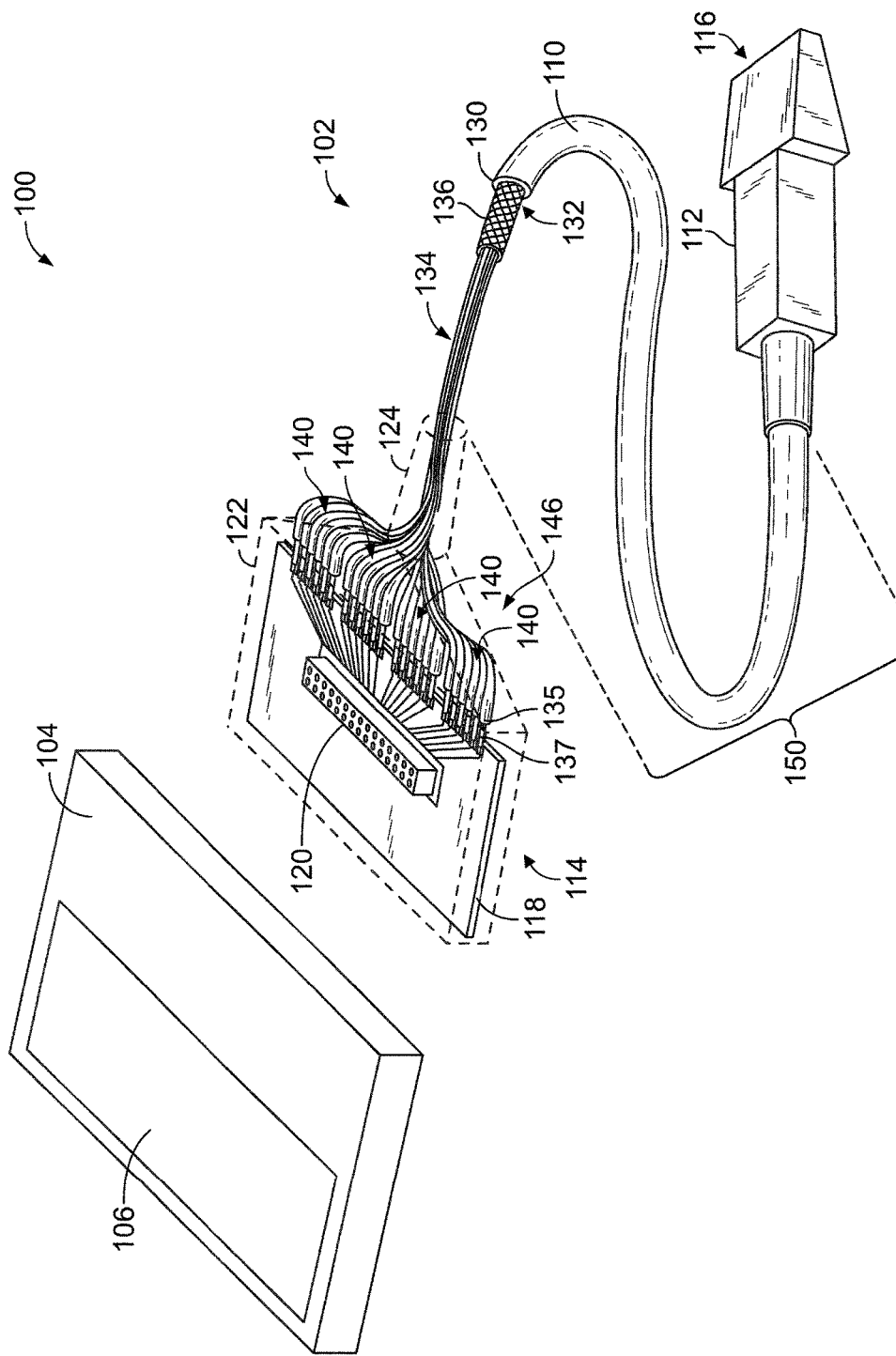
FIG. 1 is a perspective view of a system formed in accordance with an embodiment that includes a control system and a probe assembly.

Embodiments set forth herein include cable assemblies having wire pairs extending therethrough. Embodiments set forth herein also include systems and probe assemblies that include cable assemblies having such wire pairs. One conductor of the wire pair is for a forward signal and another conductor of the wire pair provides ground for the current return. As an example, an ultrasound probe may have an array of transducer elements that electrically couple to a plurality of wire pairs. For each wire pair, one conductor may be connected to a positive side of a corresponding transducer element, and the other conductor may be connected to a negative (ground) side of the corresponding transducer element. The negative (ground) sides of the different transducer elements are common, but the positive sides of the transducer elements may be isolated from one another. Each of the conductors is surrounded by insulation. The material of the insulation and the size (e.g., diameter) of the conductors may be designed to control impedance and crosstalk levels.

The wire pairs may be twisted pairs in which two insulated wires are twisted or helically wrapped about a central axis of the wire pair as the wire pair extends lengthwise through the cable assembly. The wire pairs may be shielded or unshielded and may or may not have an insulation layer (e.g., jacket) that surrounds the wire pair. In particular embodiments, the wire pairs are unshielded and do not have an insulation layer surrounding the wire pair. The twisting of the conductors helps to minimize electromagnetic interference, to maintain the same distance between the two conductors, and to ensure that certain separation between individual pairs is achieved. Although various dimensions may be used in other embodiments, particular embodiments may include twisted pairs in which each insulated wire is 42 AWG such that the twisted pair has a diameter of 0.0072 inches (or 0.18288 millimeters (mm)) having characteristic impedance of 85 Ohms.

As used herein, a "twisting rate" or "rate of twisting" is a number of helical twists in the twisted pair for a designated length. For example, a twisting rate may be between 5-7 twists/inch (or 1.97-2.76 twists/centimeter) for a 42 AWG wire pair. The twisting of the two insulated wires may occur at a uniform rate. In some embodiments, however, the twisting may occur at different rates throughout the length of the twisted pair. For example, a first segment of the twisted pair may have a twisting rate of X, a subsequent second segment may have a different twisting rate of Y, a subsequent third segment may have the twisting rate of X (or other twisting rate), and so on. Alternatively or in addition to the above, different twisted pairs may have different twisting rates. For example, a first twisted pair may have a uniform twisting rate of X, and a second twisted pair may have a different uniform twisting rate of Y. In some embodiments, the twisting rate may be optimized for durability and/or cost. For instance, as the twisting rate increases, less stress is experienced by an insulated wire when the insulated wire is bent. However, a lower twisting rate costs less to produce the wire pair.

In other embodiments, the wire pairs may be parallel pairs in which two insulated wires extend parallel to each other as the wire pair extends lengthwise through the cable assembly. Insulated wires of the parallel pair are not spaced apart. For example, two conductors may share an insulated molded jacket.

Embodiments set forth herein may have an improved performance compared to conventional cable assemblies that include coaxial conductors and/or a reduced cost compared to conventional cable assemblies that include coaxial conductors. Another technical effect of one or more embodiments may include a reduction in weight of the cable assembly compared to conventional cable assemblies that include coaxial conductors. Another technical effect of one or more embodiments may include an increase in flexibility of the cable assembly compared to conventional cable assemblies that include coaxial conductors. Another technical effect of one or more embodiments may include a reduced number of components and/or steps performed when constructing the cable assembly compared to conventional cable assemblies that include coaxial conductors. Another technical effect of one or more embodiments may include a reduced likelihood that the cable assembly (or the wire pairs) will kink, compared to conventional cable assemblies that include coaxial conductors, when the cable assembly is bent at a small radius. Another technical effect of one or more embodiments may include a higher maximum service temperature rating of the cable assembly compared to conventional cable assemblies that include coaxial conductors. It should be understood that each and every embodiment set forth herein may not have each and every technical effect provided above.

Embodiments may be configured to communicate analog or digitals signals. In some embodiments, the probe assembly is configured communicate analog signals through the wire pairs at frequencies between 0.5 MHz and 50.0 MHz and have a maximum near end crosstalk that is −26 dB or better. In particular embodiments, the probe assembly is configured to communicate analog signals through the wire pairs at frequencies between 0.5 MHz and 30.0 MHz and have a maximum near end crosstalk that is −26 dB or better. In more particular embodiments, the probe assembly is configured to communicate analog signals through the wire pairs at frequencies between 0.5 MHz and 15.0 MHz and have a maximum near end crosstalk that is −26 dB or better. Testing for crosstalk may be performed using an industry-acceptable standard (e.g., using network analyzers or oscilloscopes). Alternatively, embodiments may communicate digital signals.

FIG. 1 illustrates a system 100 formed in accordance with an embodiment that includes an assembly 102 and a control system 104 that are communicatively coupled to one another. The assembly 102 includes a cable assembly 110 and a modular device 112. In the illustrated embodiment, the modular device 112 is an ultrasound device, such as an ultrasound probe or transducer, but it is contemplated that other devices may be used. The cable assembly 110 extends between and communicatively couples the modular device 112 and the control system 104. Hereinafter, the assembly 102 will be referred to as the probe assembly.

Although the cable assembly 110 is illustrated as communicatively coupling the modular device 112 of a probe assembly 102 and the control system 104, it should be understood that the cable assembly 110 may be used for a variety of applications. In particular, the cable assembly 110 may include twisted pairs of different twists and/or wire pairs having different braided arrangements in which the insulated wires electrically couple different components. For example, the modular device 112 may include an imaging sensor (e.g., CMOS). The modular device 112 may be another type of sensor that detects external signals and communicates the external signals, directly or indirectly, to a control system 104. The sensor may also be referred to as a detector or transducer. Unless explicitly recited otherwise in the claims, the cable assemblies set forth herein are not limited to probe assemblies.

In the illustrated embodiment, the control system 104 is a portable user device having a display 106. For example, the control system 104 may be a tablet computer. In other embodiments, the control system 104 may be a laptop computer or smartphone. Yet in other embodiments, the control system 104 may be a larger control system, such as a workstation. The control system 104 (or control system) may include one or more processors (or processing units) that are configured to execute programmed instructions. For example, the control system 104 may receive data signals that are based on external signals detected by the probe assembly 102, process the data signals, and generate useful information for the user. The control system 104 may transform the data signals into images that are shown on the display 106. The display 106 may include a touch screen that is configured to receive user inputs such that a user may control operation of the system 100 through the touch screen. Alternatively or in addition to the touchscreen, the control system 104 may include an input device, such as a keyboard or touchpad, for receiving user inputs. The control system 104 may also be configured to communicatively couple to an external input device, such as a mouse or external keyboard. In some embodiments, the control system 104 may transmit signals to emit energy from a modular device 112 of the probe assembly 102.

In an exemplary embodiment, the probe assembly 102 is used for ultrasound imaging. In some embodiments, the modular device 112 may be a catheter that is configured to be inserted into a body (e.g., human or animal). For example, modular device 112 may be configured for real-time three-dimensional (3D) ultrasound imaging. Ultrasound can be excited by many different methods, including the piezoelectric effect, magnetostriction, and the photoacoustic effect.

As shown in FIG. 1, the modular device 112 is an ultrasound probe. In some embodiments, the modular device 112 may be or include a piezoelectric micromachined ultrasonic transducer (PMUT) or a capacitive micromachined ultrasonic transducer (CMUT). The modular device 112 may be or include a solid state device, such as complementary metal-oxide semiconductors (CMOSs), charge-coupled devices (CCDs), and the like. The modular device 112 may be sized for insertion into, for example, a patient's body. In some embodiments, the modular device 112 is configured to detect or observe external signals.

In other embodiments, the modular device 112 may include or constitute an imaging sensor (e.g., CMOS). The modular device 112 may also be configured to measure conditions within a designated space, such as pressure or temperature. The modular device 112 may also be configured for stimulation by delivering electrical pulses. It should be understood that the modular device 112 may also be configured for both detection and therapy in some embodiments.

The probe assembly 102 has a connector end 114, a device end 116, and the cable assembly 110 extending therebetween. The cable assembly 110 has a cable jacket 130 that defines a channel 132 that extends lengthwise along the cable jacket 130. The cable jacket 130 extends between opposite ends 131, 133 of the cable jacket 130. The cable jacket 130 may include strain relief 124 at each of the opposite ends 131, 133. The cable assembly 110 also includes a plurality of wire pairs 134 that extend through the channel 132. In the illustrated embodiment, the cable assembly 110 also includes a shield layer 136 (e.g., braided shield) that surrounds the plurality of wire pairs 134.

The connector end 114 and device end 116 are shown as examples of components that can be interconnected by the cable assembly 110. In the illustrated embodiment, the connector end 114 includes a printed circuit 118 having a system connector 120 mounted thereto for connection to the control system 104. The printed circuit 118 may be, for example, a printed circuit board (PCB) or a flex circuit. In alternative embodiments, the wire pairs 134 may be terminated directly to the control system 104. The connector end 114 also includes a housing 122.

Figure 2:
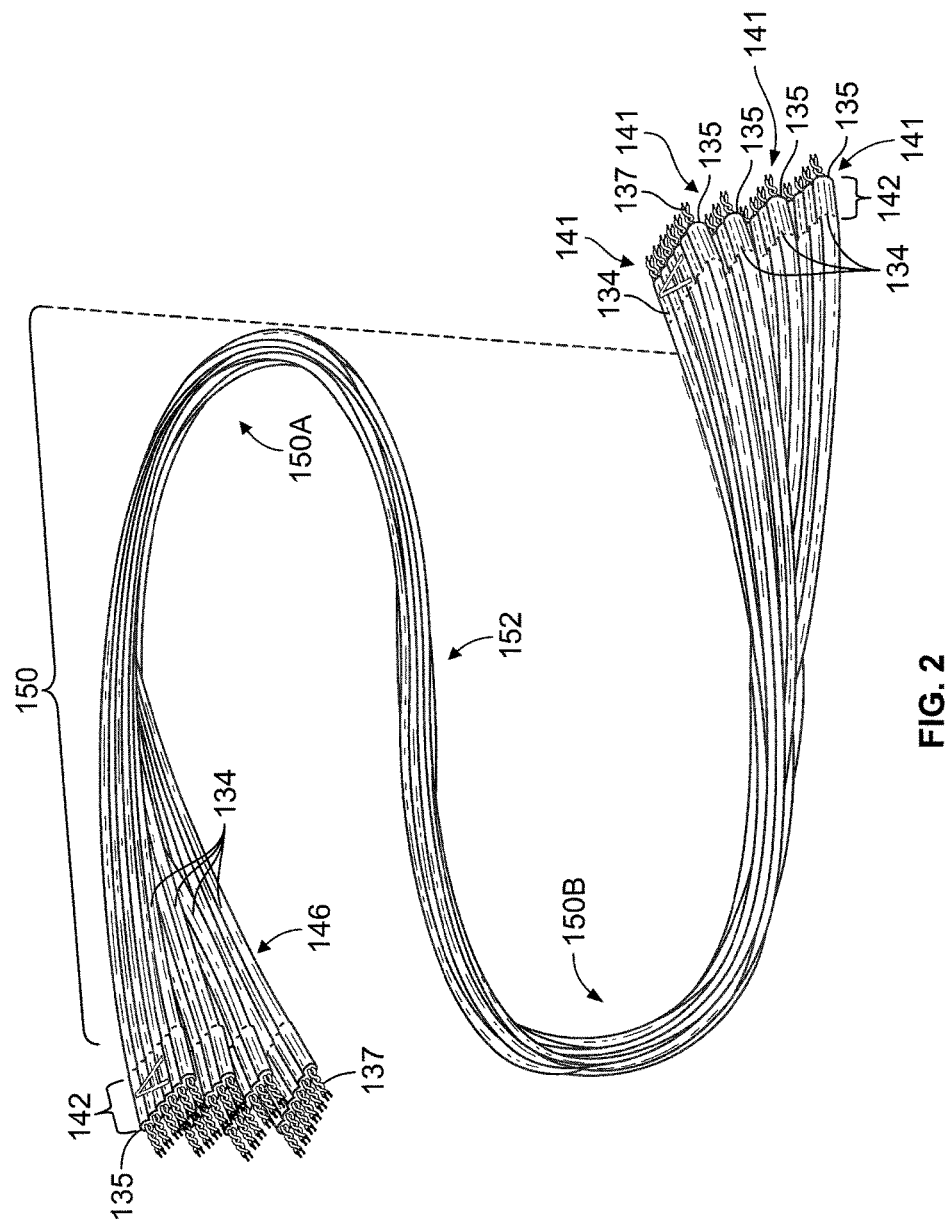
FIG. 2 is a perspective view of the cable assembly of FIG. 1 formed in accordance with an embodiment.

As shown in FIGS. 1 and 2, end portions or segments 142 of the wire pairs 134 are arranged into designated groups 140 proximate to the connector end 114 and designated groups 141 (FIG. 2) proximate to the device end 116. Arranging wire pairs into designated groups at one or both ends of the cable assembly may facilitate terminating the wire pairs to respective conductive elements (e.g., pad of printed circuit, ground plane, and the like). Each of the designated groups 140, 141 includes a plurality of the wire pairs 134. More than one group 140 may be stacked or positioned adjacent to one another at the connector end 114. Likewise, more than one group 141 may be stacked or positioned adjacent to one another at the device end 116.

The wire pairs 134 of a designated group 140 (or 141) are coupled to one another proximate to wire ends 135 of the wire pairs 134 such that the wire pairs 134 have substantially fixed positions with respect to one another proximate to the wire ends 135. The wire ends 135 include an end of insulation of the insulated wire. By way of example, the wire pairs 134 may be coupled in substantially fixed positions with respect to one another by tape (FIG. 2). Alternatively, the insulation of the wire pairs 134 of one designated group 140 may be combined such that a single section of insulation holds the conductors of the wire pairs 134 in substantially fixed positions with respect to one another proximate to the wire ends 135. The single section of insulation may correspond to the same section provided by the tape. The wire pairs 134 may separate from one another as the wire pairs 134 extend toward the other end.

It should be understood that when the wire pairs 134 are held in "substantially fixed positions with respect to one another proximate to the wire ends," the exposed conductors 137 of the insulated wires may still be manipulated (e.g., bent or moved) for terminating to a corresponding element. It should also be understood that other mechanisms exist for holding the wire pairs 134 in substantially fixed positions with respect to one another. For example, a clamp (not shown) made hold the designated group 140 (or 141) of wire pairs 134 or the designated group 140 (or 141) may be sandwiched between two housing shells (not shown). In some embodiments, the wire pairs 134 are not held in substantially fixed positions with respect to one another at the wire ends 135.

The wire pairs 134 of each of the designated groups 140 may correspond to a single designated group 140 at the other end of the cable assembly 110. In other words, each designated group 140 corresponds to one designated group 141 and only one designated group 141. In such embodiments, the wire pairs 134 may form a ribbon layer 146. FIGS. 1 and 2 show the cable assembly 110 as including four (4) ribbon layers 146. Each ribbon layer 146 has a plurality of wire pairs 134 that extend between the connector end 114 and the device end 116. The wire pairs 134 form a designated group 140 at the connector end 114 and a designated group 141 at the device end 116.

Alternatively, the wire pairs 134 of at least one designated group at one end of the cable assembly 110 may correspond to multiple designated groups at the other end. For example, two wire pairs 134 from a designated group 140 at the connector end 114 may become part of a first designated group 141 at the device end 116. Two other wire pairs 134 from the same designated group 140 may become part of a second designated group 141 at the device end 116 of the cable assembly 110.

The wire pairs 134 are typically held in substantially fixed positions at the connector end 114 and at the device end 116. A loose portion 150 of the cable assembly 110 may extend between the connector end 114 and the device end 116. The loose portion 150 includes portions of the wire pairs 134 that are permitted to move with respect to one another. As shown in FIG. 2, the loose portion 150 of the cable assembly 110 is not constrained by tape or combined insulation as described above. The wire pairs 134 are only constrained at the connector end 114 and at the device end 116. As such, the wire pairs 134 are permitted to move freely with respect to one another along the loose portion 150.

In alternative embodiments, the wire pairs 134 may also be constrained at other locations along the cable assembly 110. For example, the wire pairs 134 may be coupled together by tape at a designated point 152 along a length of the cable assembly 110. By way of example, the cable assembly may be between three feet (or 0.91 meters (m)) and twelve feet (or 3.66 m) or, more particularly, between six feet (or 1.83 m) and ten feet (3.05 m), although other lengths may be possible. In FIG. 2, the designated point 152 is a midpoint, but other locations may be used. In such embodiments, the cable assembly 110 includes two loose portions 150A, 150B. The loose portion 150A extends between the connector end 114 and the midpoint 152. The loose portion 150B extends between the device end 116 and the midpoint 152.

In some embodiments, each of the ribbon layers 146 includes a single layer of wire pairs 134. More specifically, the wire pairs 134 of the designated groups 140, 141 of each ribbon layer 146 may be coplanar with respect to one another. It is understood that the wire pairs 134 of one ribbon layer 146 may move with respect to one another along the loose portion 150. In other embodiments, however, the ribbon layer 146 may include multiple layers of wire pairs 134. For example, a designated group may include multiple rows of wire pairs 134 stacked with respect to one another. In some embodiments, the cable assembly 110 includes multiple ribbon layers 146. In other embodiments, however, the cable assembly 110 may include only a single ribbon layer 146. To facilitate assembly, the designated groups 140, 141 may be labeled (e.g., A, B, or C).

FIGS. 3A and 3B illustrate an example of a twisted pair 170 and an example of a parallel pair 180, respectively. In FIG. 3A, the twisted pair 170 includes an insulated signal wire 172 and an insulated ground wire 174. In the illustrated embodiment, each of the insulated signal wire 172 and the insulated ground wire 174 includes a wire conductor 176 and an insulation layer 178 that surrounds the wire conductor 176. In some embodiments, the wire conductors may also be referred to as magnet wires. The insulated signal wire 172 and the insulated ground wire 174 are twisted about a central axis 173 of the twisted pair 170.

As shown in FIG. 3A, the twisted pair 170 has a cross-sectional area 175 (indicated by the dashed circle). The cross-sectional area 175 is defined by a diameter 191 of the twisted pair 170. The diameter 191 is measured when viewed along the central axis 173 and represents the space occupied by the insulated wires 172, 174 as the insulated wires 172, 174 are twisted about the central axis 173. The diameter 191 may also be the maximum distance between opposite outer surfaces of the insulated wires 172, 174.

In some embodiments, the insulated signal wire 172 and the insulated ground wire 174 of a corresponding twisted pair 170 have identical dimensions. In other embodiments, as described herein, the insulated signal wire 172 and the insulated ground wire 174 of a corresponding twisted pair 170 have different dimensions. For example, the diameters of the wire conductors 176 may be different and/or a thickness of the insulation layers 178 may be different.

In FIG. 3B, the parallel pair 180 includes an insulated signal wire 182 and an insulated ground wire 184. In the illustrated embodiment, each of the insulated signal wire 182 and the insulated ground wire 184 includes a wire conductor 186. The insulated wires 182, 184 share a common insulation layer 188. The insulation layer 188 holds the wire conductors 186 of the parallel pair 180 such that the two wire conductors 186 extend parallel to one another throughout a length of the parallel pair 180.

As shown in FIG. 3B, the parallel pair 180 has a cross-sectional area 185, which may be defined by a cross-sectional profile of the parallel pair 180 at a designated cross-section. In some cases, the cross-sectional profile is essentially a rounded rectangle. In such embodiments, the cross-sectional area 185 may be defined by a height 193 and width 194 of the parallel pair 180.

FIG. 4 is a cross-section of a cable assembly 200 in accordance with an embodiment. The cable assembly 200 may be similar or identical to the cable assembly 110 (FIG. 1). The cable assembly 200 may be configured to communicatively couple a modular device (e.g., ultrasound device) and a control system (not shown in FIG. 4), although it is contemplated that the cable assembly 200 may be used for other applications. The cable assembly 200 includes a cable jacket 202, a shield layer 204, and a plurality of wire pairs 206. The wire pairs 206 form a bundle or group 207. In some embodiments, each of the wire pairs 206 in the bundle 207 is configured to transmit signals between the modular device and the control system. The cable jacket 202 may comprise, for example, an insulative material. In some embodiments, the shield layer 204 may comprise braided strands of metal (e.g., copper). In other embodiments, the shield layer 204 may comprise a tape having a metallic layer (e.g., backing) that is wrapped about the wire pairs 206.

An outer diameter 203 of the cable jacket 202 may be less than 20.0 mm. In some embodiments, the outer diameter 203 of the cable jacket 202 is less than 10.0 mm. In certain embodiments, the outer diameter 203 of the cable jacket 202 is less than 8.0 mm. In particular embodiments, the outer diameter 203 of the cable jacket 202 is less than 6.0 mm. It should be understood, however, that the outer diameter 203 may be greater than 20.0 mm or less than 6.0 mm in other embodiments.

The cable jacket 202 surrounds a channel 210 of the cable assembly 200. However, the cable jacket 202 does not necessarily define the channel 210. As shown, an inner surface 212 of the shield layer 204 essentially defines the dimensions of the channel 210. Although the channel 210 appears to have a circular profile in FIG. 4, the channel 210 may change shape when the cable assembly 200 is squeezed and/or bent. The channel 210 may be sized to hold a designated number of wire pairs 206. For example, the number of wire pairs may be at least eight (8), at least sixteen (16), at least 32, at least 64, at least 128, at least 256, at least 512, or more.

In some embodiments, the dimensions of the channel 210 and the dimensions of the cross-sectional areas of the wire pairs 206, such as the cross-sectional areas 175 and 185 shown in FIGS. 3A and 3B, respectively, may be designed so that the wire pairs 206 within the channel 210 have a designated pack ratio. The designated pack ratio is defined as $\text{Area}^{WPS}/\text{Area}^C$ in which the $\text{Area}^{WPS}$ includes a collective cross-sectional area of the wire pairs and other optional longitudinal elements and the $\text{Area}^C$ is equal to a cross-sectional area of the channel that is accessible to (or available for moving into) the wire pairs. The collective cross-sectional area of the wire pairs 206 may include a sum of the cross-sectional areas of the wire pairs 206, such as the cross-sectional areas 175 and 185. The $\text{Area}^{WPS}$ represents the collective cross-sectional area of elements within the channel 210.

Gases and filler liquid do not form part of the $\text{Area}^{WPS}$. $\text{Area}^C$ is the available space that the wire pairs from the bundle are permitted to move within. The space in which the gases or filler liquid are disposed may be part of the $\text{Area}^C$. As an example, the $\text{Area}^C$ may be between 0.005 in$^2$ (or 0.032 cm$^2$) and 2.0 in$^2$ (or 12.9 cm$^2$). In particular embodiments, the $\text{Area}^C$ may be between 0.007 in$^2$ (or 0.045 cm$^2$) and 1.5 in$^2$ (or 9.68 cm$^2$). In more particular embodiments, the $\text{Area}^C$ may be between 0.008 in$^2$ (or 0.051 cm$^2$) and 1.0 in$^2$ (or 6.45 cm$^2$). It should be understood, however, that the $\text{Area}^C$ may have other values. In some embodiments, the elements within the channel 210 are only the wire pairs 206. In other embodiments, the elements within the channel 210 include the wire pairs 206 and other wires (e.g., for transmitting power or other communications) and spacers.

In other embodiments, however, the cable assembly 200 includes additional longitudinal elements. By way of example, the other longitudinal elements (or elongated elements that extend lengthwise through the channel 210) may include at least one of optical fibers 216, non-conductive spacers 218, or other electrical conductors 214. The other electrical conductors 214 may provide, for example, electrical power to the modular device (not shown) or may communicate data signals that differ from those communicated by the wire pairs 206. The electrical conductors 214 may also include shielded wires or coaxial conductors. The optical fibers 216 may communicate data signals between different elements, and the spacers 218 may separate the longitudinal elements within the channel 210.

In some embodiments, the other longitudinal elements 214, 216, and 218 are configured to extend through and separate the wire pairs 206. The other longitudinal elements 214, 216, and 218 may be distributed within the channel 210 for this purpose. Yet in other embodiments, the other longitudinal elements 214, 216, and 218 may be grouped together to occupy a single cable-shaped region (not shown) within the channel 210. In such embodiments, the available space within the channel 210 for the wire pairs 206 to move within is reduced.

In some embodiments, the wire pairs that are configured to transmit signals (e.g., analog ultrasound signals) may account for at least 50% of the $Area^{WPS}$. In certain embodiments, the wire pairs may account for at least 65% of the $Area^{WPS}$ or, more particularly, at least 75% of the $Area^{WPS}$. In particular embodiments, the wire pairs 06 may account for at least 80% of the $Area^{WPS}$ or, more particularly, at least 85% of the $Area^{WPS}$. In more particular embodiments, the wire pairs may account for at least 90% of the $Area^{WPS}$ or, more particularly, at least 95% of the $Area^{WPS}$.

In some embodiments, the channel may narrow at certain points along the cable assembly such that the wire pairs have a greater pack ratio at these points. However, the channel may permit the designated pack ratio to occur for a substantial portion of the length. In some embodiments, the designated pack ratio exists for at least 50% of the length of the channel, which extends between the opposite ends of the cable jacket. In certain embodiments, the designated pack ratio exists for at least 60% of the length of the channel or, more particularly, at least 75% of the length of the channel. In particular embodiments, the designated pack ratio exists for at least 80% of the length of the channel or, more particularly, at least 85% of the length of the channel. In more particular embodiments, the designated pack ratio exists for at least 90% of the length of the channel or, more particularly, at least 95% of the length of the channel.

Optionally, the cable assembly 200 may include an electrically-lossy or dissipative material disposed within the channel 210. The electrically-lossy material may be a liquid or gel that permits movement of the insulated wires. For example, the electrically-lossy material may be formed using a dielectric material with conductive particles (or fillers) dispersed within the dielectric material. The dielectric material, such as a polymer or epoxy, may be used as a binder to hold the conductive particle filler elements in place. Although the conductive particles are conductive, the conductive particles may impart loss to the conductive material. Electrically-lossy material may be only partially conductive compared to, for example, the wire conductors.

As one example, the conductive material prior may comprise carbon, graphite, graphene, silver, or copper, and may be in a suspended solution. For example, Dag 502 (also known as Electrodag 502), carbon/graphite particles in a fluoropolymer binder suspended in methylethylketone, may be used. Examples of conductive particles that may be used as a filler to form electrically-lossy materials include carbon or graphite formed as fibers, flakes, or other particles. Metal in the form of powder, flakes, fibers, or other conductive particles may also be used to provide suitable electrically-lossy properties. Alternatively, combinations of fillers may be used.

The designated pack ratio corresponds to a density of the wire pairs 206 within the channel 210 and may determine a level of constraint for the wire pairs 206 within the channel 210. By way of example, the designated pack ratio may be at most 0.90. In some embodiments, the designated pack ratio may be at most 0.80 or at most 0.70. Yet in more particular embodiments, the designated pack ratio may be at most 0.60, at most 0.50, at most 0.40, or at most 0.30.

In some embodiments, the designated pack ratio may be at least 0.05. In particular embodiments, the designated pack ratio may be at least 0.10, at least 0.20, at least 0.30, or at least 0.40. In more particular embodiments, the designated pack ratio may be at least 0.50, at least 0.60, or at least 0.70.

Embodiments may also have designated pack ratios that are within certain ranges. The ranges may be defined between the upper limits and the lower limits described above. For example, the designated pack ratio may be between 0.10 and 0.90. More particularly, the designated pack ratio may be between 0.20 and 0.80 or, more particularly, between 0.20 and 0.70. In certain embodiments, the designated pack ratio may be between 0.30 and 0.70 or, more particularly, between 0.45 and 0.65. However, it should be understood that embodiments may have designated pack ratios found within other ranges.

As the designated pack ratio decreases, space increases within the channel 210 that permits the wire pairs 206 to move relative to one another therein when the cable assembly 200 is moved. A larger channel also allows each of the wire pairs 206 to have more meandering paths through the channel 210 such that the wire pairs 206 do not extend adjacent to a small number of adjacent wire pairs 206 throughout the length. Crosstalk between two wire pairs may be a function of the distance between the two wire pairs and the length at which the two wire pairs extend adjacent to each other through the cable assembly. Crosstalk increases as the wire pairs become closer and as the distance at which the wire pairs extend alongside each other increases. A greater amount of space may (a) permit greater gaps to exist between two adjacent wire pairs and (b) allow these two wire pairs to have more meandering paths so that the two wire pairs have shorter distances at which the two wire pairs extend sufficiently adjacent to each other to develop crosstalk.

The channel represents the available space in which the wire pairs, along with other optional longitudinal elements, may exist within the cable assembly during usage of the cable assembly. If space within the channel is not accessible to the wire pairs, then the space is not available space and is not used in calculating a designated pack ratio. For example, if the cable jacket includes an inner lumen or a partition wall extending through a center of the cable jacket and the wire pairs can exist only outside the inner lumen or only one side of the partition wall, the available space for determining the pack ratio is the space through which the wire pairs can extend. Any space that the wire pairs cannot extend (e.g., due to the inner lumen or the partition wall) is not considered space for determining the pack ratio.

If wire pairs exist on both sides of the partition wall (or within and outside the inner lumen), however, each channel may have a respective pack ratio. Based on the application of the cable assembly, it is possible that a less dense pack ratio is not desirable for each channel. As such, the claims do not require each channel to satisfy the designated pack ratio unless the claims specifically recite "each and every channel through the cable jacket" having a designated pack ratio.

During usage of the cable assembly, one or more sharp bends may exist due to how the probe is positioned by the user. At a sharp bend, the cable jacket may be deformed and/or the longitudinal elements may be compressed or tightly bunched with respect to one another. Nonetheless, a majority of the cable jacket may not be bent sharply such that greater gaps between wire pairs are permitted and/or more meandering paths of the wire pairs are permitted. As such, the designated pack ratio is determined using the $Area^C$ when the cable jacket is not bent such that the channel shape is distorted. Although the $Area^C$ is circular in the illustrated embodiment, the $Area^C$ is not required to be circular and may have other shapes (e.g., oval-shaped, semi-circular, etc.). If any longitudinal elements are compressible (e.g., foam spacers), the cross-sectional area for those longitudinal elements when calculating the pack ratio is the cross-sectional area of the longitudinal element when not compressed beyond the condition of the longitudinal element within the channel.

Moreover, when the cable assembly 200 is relatively motionless, the space may allow the wire pairs 206 to generally disperse or move away from one another. For example, when the wire pairs 206 are tightly packed (e.g., a high pack ratio greater than 0.80), the insulation layers of adjacent wire pairs 206 may be compressed at certain segments of the cable assembly 110. When the pack ratio is smaller, the insulation layers of the wire pairs become less compressed. The wire pairs 206 may become more evenly distributed within the channel 210.

In particular embodiments, the wire pairs 206 are twisted pairs, such as the twisted pair 170 (FIG. 3A). In particular embodiments, the wire pairs 206 are parallel pairs, such as the parallel pair 180 (FIG. 3B).

As described herein, the space existing between the wire pairs may be occupied by empty space (e.g., one or more gases) or a filler liquid having a viscosity that permits movement. The gases and/or filler liquids may be selected to permit a designated range of movement for the wire pairs. The gases and/or filler liquids may be selected to enable a designated performance for the probe assembly or the cable assembly. For example, the cable assembly may be configured to communicate analog signals through the wire pairs at frequencies between 0.5 MHz and 50.0 MHz and a maximum near end crosstalk may be −26 dB or better. In either case, the empty space or the filler liquid permits the wire pairs to move. The filler liquid is essentially incompressible, thereby permitting the wire pairs to move. In some embodiments, the filler liquid may be characterized as a gel (e.g., silicone gel). In some embodiments, the filler liquid may be conductive.

The channel 210 is circular and has a channel diameter 211. For some embodiments, the channel diameter 211 may be less than 15.0 mm. In certain embodiments, the outer diameter 203 of the cable jacket 202 is less than 5.0 mm. In particular embodiments, the outer diameter 203 of the cable jacket 202 is less than 4.0 mm. In more particular embodiments, the outer diameter 203 of the cable jacket 202 is less than 3.0 mm. It should be understood, however, that the outer diameter 203 may be greater than 15.0 mm or less than 3.0 mm in other embodiments.

The pack ratio may be determined by calculating the $Area^C$ using the channel diameter 211 and then summing the cross-sectional areas of the various longitudinal elements (e.g., wire pairs, other conductors, and spacers) that share the available space of the channel 210 to provide the $Area^{WPS}$.

Figure 5:
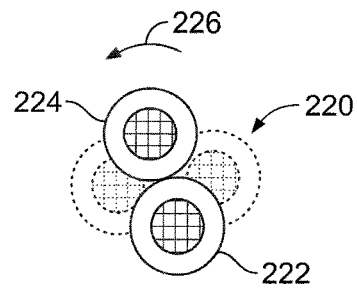
FIG. 5 illustrates a cross-section of a first twisted pair in which the two insulated wires are twisted about each other in a first direction.
Figure 6:
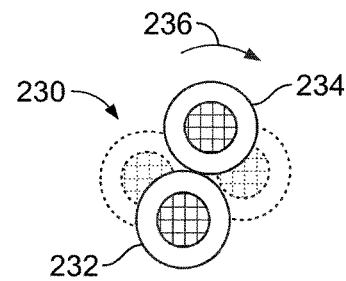
FIG. 6 illustrates a cross-section of a second twisted pair in which the two insulated wires are twisted about each other in an opposite second direction.

FIGS. 5 and 6 illustrate cross-sections of a first twisted pair 220 and a second twisted pair 230, respectively. For the first twisted pair 220, two insulated wires 222, 224 are twisted about each other or twisted about a central axis in a first direction (indicated by arrow 226). For the perspective shown in FIG. 5, the first direction 226 is a counter-clockwise direction. For the second twisted pair 230, however, two insulated wires 232, 234 are twisted about each other or twisted about a central axis in a second direction (indicated by arrow 236). For the perspective shown in FIG. 6, the second direction 236 is a clockwise direction.

Figure 7:
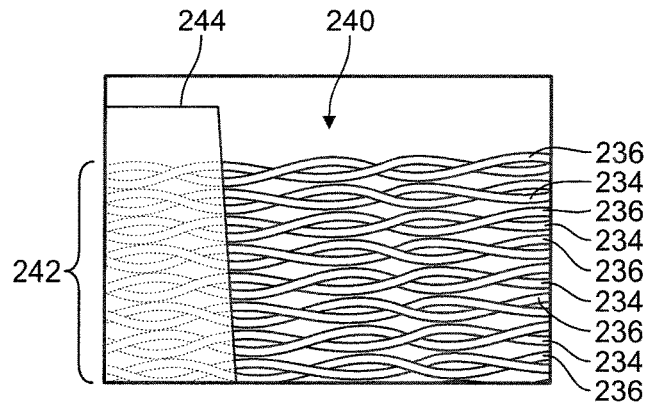
FIG. 7 is an enlarged perspective view of a portion of a cable assembly in which the first and second twisted pairs of FIGS. 5 and 6 are arranged in a designated manner.

FIG. 7 is an enlarged perspective view of a portion of a cable assembly 240 in which the first and second twisted pairs 220, 230 are arranged in a designated manner. More specifically, the first and second twisted pairs 220, 230 are coupled to one another in a designated group 242. For example, the cable assembly 240 includes tape 244 that is adhered to the twisted pairs 220, 230 of the designated group 242. The first and second twisted pairs 220, 230 of the designated group 242 are coplanar such that a single layer is formed. In other embodiments, however, the first and second twisted pairs 220, 230 of the designated group 242 are not required to form a single layer. For example, the first and second twisted pairs 220, 230 may be positioned side-by-side along one dimension and then stacked onto one another in a perpendicular direction. This stacked arrangement may then be wrapped with tape, such as the tape 244.

Alternatively, the stacked arrangement may be positioned within a cavity of a mold and melted material may be injected into the cavity and allowed to surround the stacked arrangement and seep between adjacent wire pairs. The melted material may be allowed to cure to form the designated group 242 of first and second twisted pairs 220, 230.

The first and second twisted pairs 220, 230 may be positioned to have an alternating arrangement with respect to one another. For example, each first twisted pair 220 may be positioned between two second twisted pairs 230 and each second twisted pair 230 may be positioned between two first twisted pairs 220. If the first twisted pair 220 or second twisted pair 230 is positioned at a flank of the designated group 242, the corresponding twisted pair may only be positioned next to one twisted pair of the other twist direction.

However, the term "alternating arrangement" does not require the first and second twisted pairs alternating every other one. As used herein, the term "alternating arrangement" includes the first twisted pairs and the second twisted pairs being substantially evenly distributed with respect to one another at the designated region and/or within the designated group. For example, the first and second twisted pairs 220, 230 may have an alternating arrangement at a connector end (not shown) or at a device end (not shown) of the cable assembly 240 in which the first and second twisted pairs 220, 230 are coupled together in the designated group 242.

As another example, a first ribbon layer having only first twisted pairs may be stacked onto a second ribbon layer at the connector end and also stacked onto the second ribbon layer at the device end. The second ribbon layer may have only second twisted pairs. In some embodiments, the designated pack ratio of the cable assembly and/or the twist orientation of the ribbon layers may permit the twisted pairs of the corresponding first and second ribbon layers to interweave with one another as the twisted pairs extend between the connector end and the device end. In such embodiments, the twisted pairs for a majority of the length may form an alternating arrangement such that the twisted pairs of different twist orientations are substantially evenly distributed with respect to one another. In some embodiments, the alternating arrangement includes at least one of: (a) each first twisted pair being adjacent to at least one second twisted pair or (b) each second twisted pair being adjacent to at least one first twisted pair.

In some embodiments, the first twisted pairs and the second twisted pairs are interspersed within the channel. For example, when viewing a cross-section of the cable assembly at or near a midpoint of the cable jacket, each first twisted pair may be adjacent to at least one second twisted pair and each second twisted pair may be adjacent to at least one first twisted pair.

In some embodiments, the first twisted pairs and the second twisted pairs have about an equal amount within the channel (e.g., about 1:1 ratio). However, other embodiments may not have an equal number. For example, a ratio of the first twisted pairs to the second twisted pairs may be between or including 4:1 or 1:4. In some embodiments, a ratio of the first twisted pairs to the second twisted pairs may be between or including 3:1 or 1:3. In certain embodiments, a ratio of the first twisted pairs to the second twisted pairs may be between or including 2:1 or 1:2. In particular embodiments, a ratio of the first twisted pairs to the second twisted pairs may be between or including 5:4 or 4:5.

Figure 8:
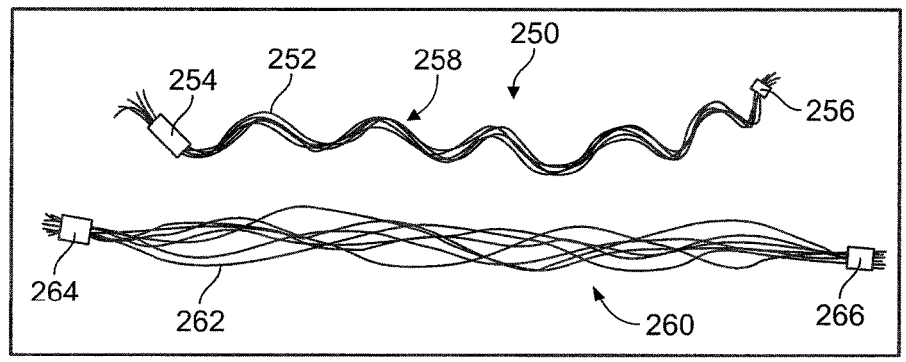
FIG. 8 illustrates a cable assembly in accordance with an embodiment in which the twisted pairs of the cable assembly have a common twist and another cable assembly in accordance with an embodiment in which some of the twisted pairs of the cable assembly are twisted in a first direction and some of the twisted pairs are twisted in an opposite second direction.

FIG. 8 illustrates a cable assembly 250 and a cable assembly 260 positioned near each another for comparison. The cable assembly 250 includes twisted pairs 252 that are coupled together as a designated group at one end by tape 254 and coupled together as a designated group at the opposite end by tape 256. The twisted pairs 252 have the same orientation in FIG. 8. For example, each and every twisted pair 252 in the cable assembly 250 has the twist orientation shown in FIG. 5. As shown, the twisted pairs 252 collectively form a helical bundle 258 in which a majority of the twisted pairs 252 group together and extend alongside each other along a helical path.

The cable assembly 260 includes twisted pairs 262 in which some of the twisted pairs 262 have a first twist orientation and some of the twisted pairs 262 have a second twist orientation. The twisted pairs 262 are coupled together as a designated group at one end by tape 264 and coupled together as a designated group at the opposite end by tape 266. As shown, the twisted pairs 262 do not form a helical bundle like the helical bundle 258. Instead, the twisted pairs 262 appear to be more evenly distributed or dispersed.

By positioning twisted pairs of different orientations in a predetermined manner at the connector end and/or the device end of the cable assembly, embodiments may reduce the likelihood that the twisted pairs will come together in a helical bundle. Such embodiments may improve an ergonomic response of the cable assembly. For example, cable assemblies that include the helical bundle may resist torque in one direction but not resist torque in another direction. As such, a user of the cable assembly may not experience a consistent response when the cable assembly is moved, which may increase frustration or cause imprecise movement of the cable assembly by the user. It is also contemplated that the helical bundles may increase crosstalk because some conductors may be forced closer to one another.

Notwithstanding the above, embodiments set forth herein are not limited to cable assemblies including twisted pairs with different twist orientations. It is possible that other embodiments may be configured to mitigate any unwanted effects of a helical bundle and/or the helical bundle may not cause a significant amount of resistance and/or crosstalk. Accordingly, unless explicitly recited in the claims, embodiments are not required to have twisted pairs with different twist orientations.

In an alternative embodiment, a first ribbon layer having only first twisted pairs and a second ribbon layer having only second twisted pairs may extend through the channel of the cable assembly. In this example, the twisted pairs of the first and second ribbon layers do not substantially interweave or do not have any interweaving. It is contemplated that the first and second ribbon layers, each having twisted pairs with a different twist direction, may still impede development of a helical bundle and/or mitigate the unwanted effects of a helical bundle.

It should also be noted that the twisted pairs 262 are not required to have an equal number of first orientation twisted pairs and second orientation twisted pairs. For example, the twisted pairs 262 may include 80% first orientation twisted pairs and 20% second orientation twisted pairs. In other embodiments, the twisted pairs 262 may include 60% first orientation twisted pairs and 40% second orientation twisted pairs. In other embodiments, however, the twisted pairs 262 may include an equal number of first orientation twisted pairs and second orientation twisted pairs.

Figure 9:
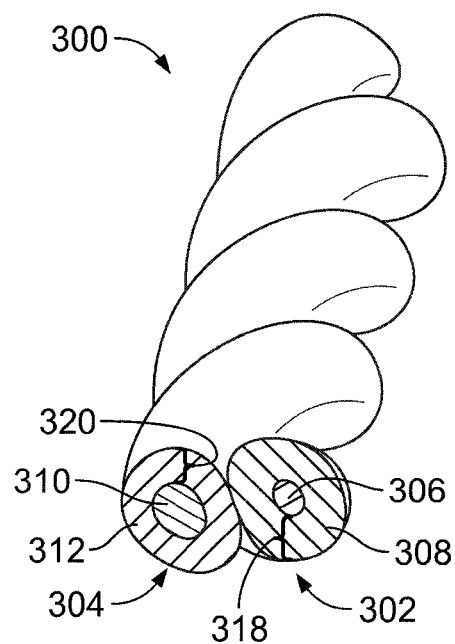
FIG. 9 illustrates a section of a twisted pair in which the two insulated wires of the twisted pair have different cross-sectional profiles.
Figure 10:
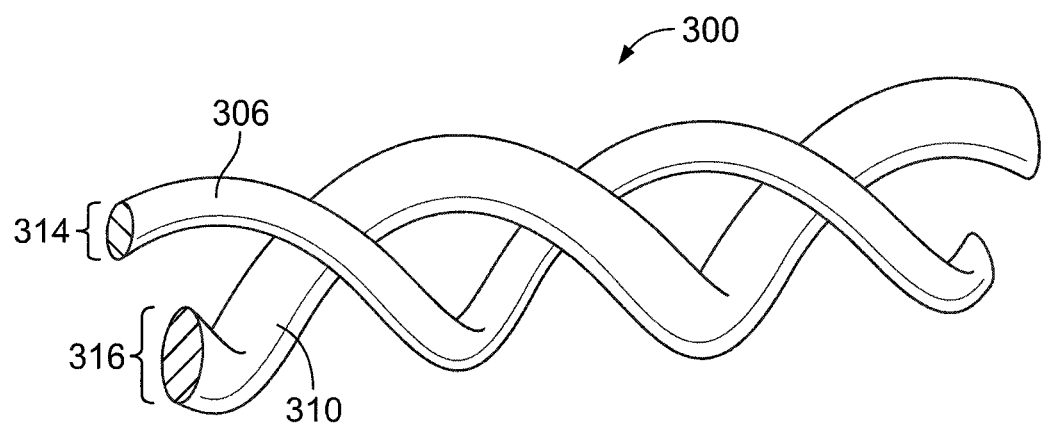
FIG. 10 illustrates the twisted pair of FIG. 9 in which the signal and ground conductors of the twisted pair have different cross-sectional profiles.

FIG. 9 illustrates a section of a twisted pair 300. The twisted pair 300 includes an insulated signal wire 302 and an insulated ground wire 304. The insulted signal wire 302 has a wire conductor (or signal conductor) 306 that is surrounded by an insulation layer 308. The insulted ground wire 304 has a wire conductor (or ground conductor) 310 that is surrounded by an insulation layer 312. FIG. 10 illustrates the twisted pair 300 in which the insulation layers 308, 312 (FIG. 9) have been removed and only the signal and ground conductors 306, 310 of the twisted pair 300 are shown.

As shown in FIGS. 9 and 10, the signal and ground conductors 306, 310 may have different cross-sectional dimensions. More specifically, the signal conductor 306 has a diameter 314, and the ground conductor 310 has a diameter 316. The diameter 316 is greater than the diameter 314. As shown in FIG. 9, the insulation layer 308 has a radial thickness 318, and the insulation layer 312 has a radial thickness 320. The radial thickness 318 is greater than the radial thickness 320. As shown in FIG. 9, the insulated signal wire 302 and the insulated ground wire 304 have the same outer diameter defined by the insulation layers 308, 312.

Accordingly, the wire conductor 310 of the insulated ground wire 304 has a first cross-sectional area 316, and the wire conductor 306 of the insulated signal wire 302 has a second cross-sectional area 314. The first cross-sectional area is greater than the second cross-sectional area.

Figure 11:
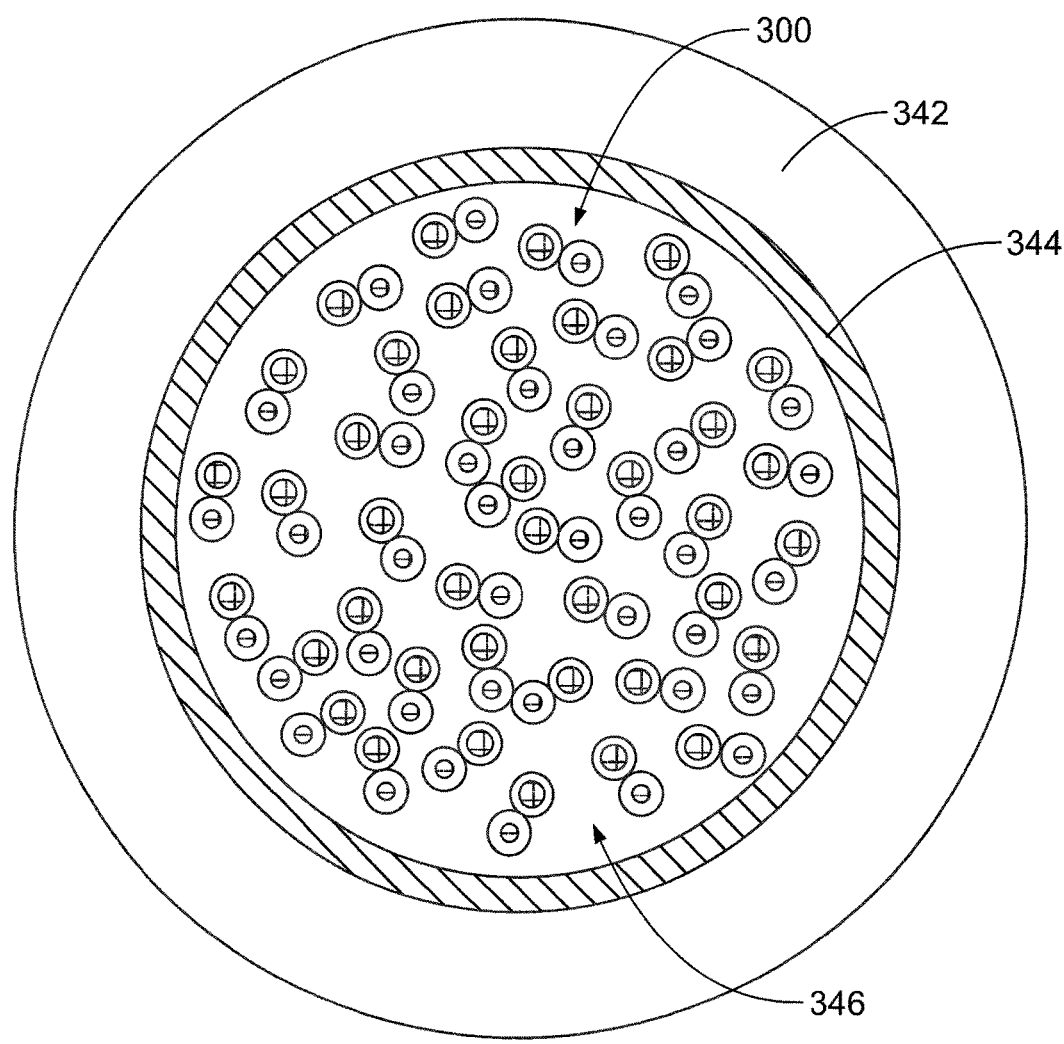
FIG. 11 is a cross-section of a cable assembly having a plurality of the twisted pairs shown in FIG. 10. The twisted pairs may be twisted in a common direction or some of the twisted pairs may be twisted in a first direction and some of the twisted pairs may be twisted in an opposite second direction.

FIG. 11 is a cross-section of a cable assembly 340 having a plurality of the twisted pairs 300. The twisted pairs 300 may be twisted in a common direction or some of the twisted pairs 300 may be twisted in a first direction and some of the twisted pairs 300 may be twisted in an opposite second direction. The cable assembly 340 may be similar to the cable assembly 200 (FIG. 4) and include a cable jacket 342 and a shield layer 344 that surround a channel 346. In some embodiments, the channel 346 and the twisted pairs 300 are designed to have a designated pack ratio that is less than 0.80. The designated pack ratio may have the lower limits, upper limits, and ranges as described above.

Returning to FIGS. 9 and 10, the insulated signal wire 302 and the insulted ground wire 304 form an asymmetric twisted pair 300. In some embodiments, the asymmetry between the insulated signal wire 302 and the insulted ground wire 304 may reduce crosstalk as the larger insulated ground wire 304 may cause the insulated signal wires 302 of adjacent twisted pairs 300 to be spaced further apart. Moreover, the diameters and radial thicknesses of the twisted pair 300 may be selected to improve impedance and attenuation control of the twisted pair 300. In addition to the above, the insulated ground wire 304 may be easier to manipulate, due to the thicker ground conductor 310, and easier to terminate, due to the thinner insulation layer 312. For example, the insulated ground wires 304 may be terminated as a group to a ground plane by simultaneously melting away the insulation layers 312. Because the insulated signal wires 302 have a greater radial thickness 318, the signal conductors 306 are more protected and less likely to be exposed during this termination process.

Figure 12:
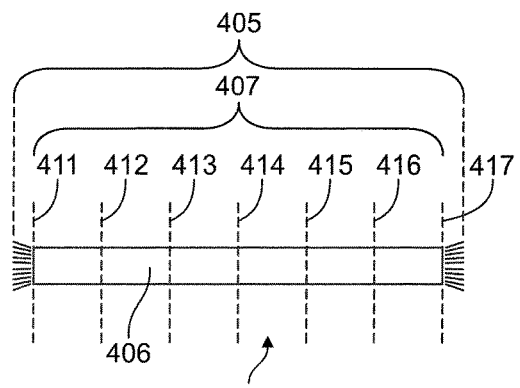
FIG. 12 is a side view of a cable assembly formed in accordance with an embodiment that identifies locations of cross-sections of the cable assembly.
Figure 13:
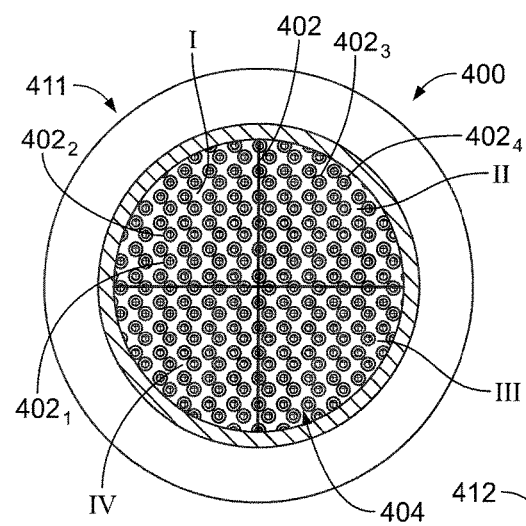
FIG. 13 illustrates one of the cross-sections located in FIG. 12.
Figure 14:
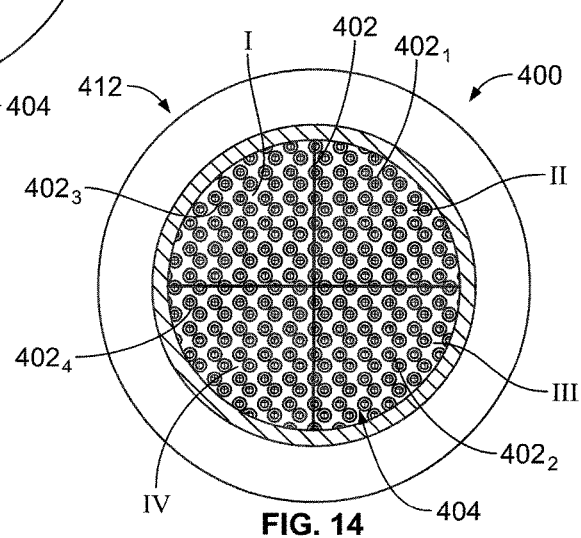
FIG. 14 illustrates a different one of the cross-sections in FIG. 12 in which the wire pairs in the cable assembly have different cross-sectional arrangements in FIGS. 13 and 14.

FIG. 12 is a side view of a cable assembly 400 formed in accordance with an embodiment. FIGS. 13 and 14 show different cross-sections of the cable assembly 400. The cable assembly 400 includes wire pairs 402 extending through a channel 404 of the cable assembly 400. The cable assembly 400 has a cable jacket 406. The cable assembly 400 has a length 405. The wire pairs 402 may be twisted pairs or parallel pairs. Optionally, the wire pairs 402 are twisted pairs in which some of the twisted pairs have a first twist orientation and some of the twisted pairs have a second twist orientation as described above. Optionally, the wire pairs 402 are asymmetric twisted pairs in which the insulated signal wire and insulated ground wires have different dimensions.

Unlike the cable assembly 200 (FIG. 4), however, the cable assembly 400 may have a designated pack ratio that exceeds 0.80. For example, the designated pack ratio may be greater than 0.85 or greater than 0.88 or greater than 0.90. In some embodiments, the designated pack ratio is configured such that the wire pairs 402 are unable to change relative positions with respect to each other when the cable assembly 400 is moved. More specifically, the channel 404 may be dimensioned such that the wire pairs 402 at a designated cross-section of the cable assembly 400 are unable to substantially move with respect to one another. As such, the wire pairs 402 at the designated cross-section will essentially always remain adjacent to the same wire pairs 402 at the designated cross-section throughout operation of the cable assembly 400.

The cable assembly 400 may be configured to reduce crosstalk from adjacent wire pairs 402 by positioning the wire pairs 402 relative to one another in a substantially predetermined manner. In some embodiments, the wire pairs 402 may be have a braided configuration in which the wire pairs 402 are interweaved. The cable jacket 406 may be extruded or overmolded around the wire pairs 402 as the wire pairs 402 are interweaved or after the wire pairs 402 are interweaved. In some embodiments, the wire pairs 402 may be interweaved in a designated manner such that near end crosstalk does not exceed a target amount during operation of the cable assembly 400.

FIG. 12 illustrates where designated cross-sections 411-417 of the cable assembly 400 are located. FIG. 13 illustrates the designated cross-section 411 of the cable assembly 400, and FIG. 14 illustrates the designated cross-section 412 of the cable assembly 400. By interweaving the wire pairs 402 in a predetermined manner, gaps between two wire pairs 402 may be changed and the wire pairs 402 may be configured to have different paths relative to other wire pairs 402. As such, any two wire pairs 402 may have shorter distances in which the two wire pairs 402 extend sufficiently adjacent to each other to develop crosstalk.

Each of the cross-sections 411, 412 of the cable assembly 400 have different cross-sectional arrangements. The cross-sectional arrangements of the cross-sections 411, 412 are essentially fixed. For example, each of the wire pairs 402 at the cross-section 411 may have a substantially fixed position with respect to the other wire pairs 402 at the cross-section 411. Each of the wire pairs 402 at the cross-section 412 may have a substantially fixed position with respect to the other wire pairs 402 at the cross-section 412. The fixed positions of the wire pairs 402 may have respective relative addresses.

A cross-sectional arrangement of wire pairs is defined by the relative addresses or relative positions of each wire pair with respect to the other wire pairs at the cross-section. Two cross-sectional arrangements are different if the wire pairs have different relative addresses or relative positions. As used herein, the terms "relative address" or "relative position" acknowledge that insubstantial movements of the wire pairs may occur during operation of the cable assembly 400. Nonetheless, the wire pairs 402 may not change relative addresses or relative positions at the cross-section. For example, a wire pair 402 that is surrounded by six adjacent wire pairs 402 will always be surrounded by those six adjacent wire pairs 402 at the cross-section although the wire pair 402 may move an insubstantial amount during operation.

However, due to the interweaving of the wire pairs 402, the cross-sectional arrangements at the first cross-section 411 and at the second cross-section 412 are different. For example, wire pairs $402_1$ and $402_2$ in a first quadrant I of the cross-section 411 have been moved into the second and third quadrants II, III, respectively, of the cross-section 412. Wire pairs $402_3$ and $402_4$ in a second quadrant II of the cross-section 411 have been moved into the first quadrant I and the fourth quadrant IV, respectively, of the cross-section 412. It is noted that the above examples are provided for illustrative purposes, and it should be understood that various cross-sectional arrangements may be formed through interweaving the wire pairs 402.

Figure 15:
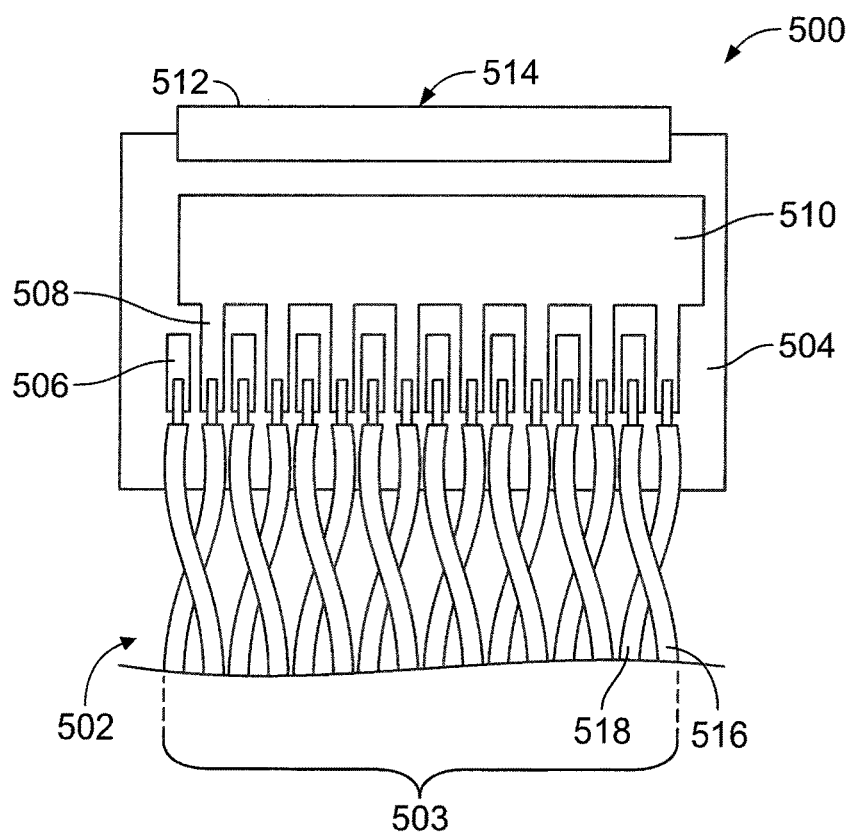
FIG. 15 is a plan view of a sub-assembly that may be used to communicatively couple the wire pairs to other components.
Figure 16:
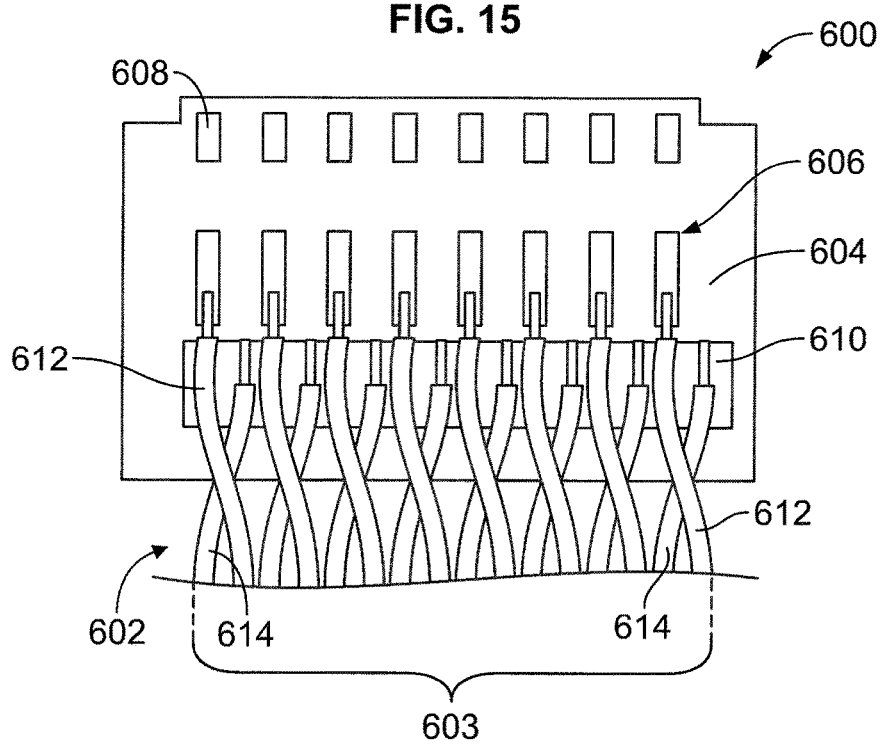
FIG. 16 is a plan view of a sub-assembly that may be used to communicatively couple the wire pairs to other components.

FIGS. 15 and 16 illustrate plan views of communication sub-assemblies 500 and 600, respectively. The sub-assemblies 500, 600 provide a termination zone for wire pairs 502, 602, respectively. As such, the sub-assemblies 500, 600 may be referred to as termination sub-assemblies. The wire pairs 502, 602 may form respective ribbon layers 503, 603. In the illustrated embodiments, the wire pairs 502, 602 are twisted pairs. In other embodiments, however, the wire pairs may be parallel pairs. In some embodiments, the communication sub-assembly 500 and/or the communication sub-assembly 600 may form part of a cable assembly, such as the cable assembly 110 (FIG. 1). The communication sub-assemblies 500, 600 may be positioned at, for example, a device end or a connector end of the cable assembly. The communication sub-assemblies 500, 600 may be disposed within a housing of a modular device, such as the modular device 112 (FIG. 1) or a housing of the connector end.

As shown in FIG. 15, the communication sub-assembly 500 includes a printed circuit 504 having a plurality of electrical contacts 506, 508 (e.g., contact pads or traces) exposed along a surface of the printed circuit 504. The printed circuit 504 may include a flexible circuit or a printed circuit board (PCB) or a combination thereof. The electrical contacts 506, 508 include signal contacts 506 and ground contacts 508. The ground contacts 508 are electrically coupled to a ground plane 510 of the printed circuit 504. As shown, the electrical contacts 508 and the ground plane 510 are portions of a common metal layer. In other embodiments, however, the ground contacts 508 and the ground plane 510 may be positioned at different layers and interconnected through, for example, vias. The wire pairs 502 are terminated to the printed circuit 504. More specifically, insulated signal wires 516 are terminated to the electrical contacts 506, and insulated ground wires 518 are terminated to the electrical contacts 508. The wires may be terminated by, for example, soldering, welding, or bonding.

Optionally, the communication sub-assembly 500 includes an electrical connector 512, such as a board-to-board connector. The electrical connector 512 may have a mating interface 514 that is configured to mechanically and electrically couple to another component (not shown), such as another electrical connector. The mating interface 514 may have electrical contacts that are designed (e.g., sized, shaped, and positioned) to engage corresponding electrical elements of the other component.

In other embodiments, however, the communication sub-assembly 500 does not include an electrical connector 512. For example, the printed circuit 504 may be a flex circuit having exposed pads that are configured to form flex-to-flex bonds with pads of another printed circuit. Such an example is shown in FIG. 16.

The communication sub-assembly 600 of FIG. 16 includes a printed circuit 604 having electrical contacts 606 (e.g., contact pads or traces) exposed along a surface of the printed circuit 604. The printed circuit 604 may include a flexible circuit or a printed circuit board (PCB) or a combination thereof. The electrical contacts 606 are signal contacts and are electrically coupled to electrical contacts 608 that are positioned along an edge of the printed circuit 604. The electrical contacts 608 are configured to be electrically coupled (e.g., through bonding) to another electrical component.

The electrical contacts 606 are positioned adjacent to a ground plane 610 that is also exposed along the surface of the printed circuit 604. The wire pairs 602 include insulated signal wires 612 and insulated ground wires 614. The insulated signal wires 612 are configured to be electrically coupled to corresponding electrical contacts 606. The insulated ground wires 614 are configured to be electrically coupled to the ground plane 610.

In some embodiments, the wire pairs 602 are similar or identical to the asymmetric twisted pair 300 (FIG. 9) in which the insulation layers of the insulated wires have different thicknesses. In such embodiments, the insulation of the insulated ground wires 614 has a smaller thickness than an insulation of the insulated signal wires 612. In one method of terminating the ground conductors, the insulation of the insulated ground wires 614 may be simultaneously melted by a hot plate and the group of insulated ground wires 614 may be pressed onto the ground plane 610. If the hot plate contacts the insulation of the signal wires 612, the greater thickness of the insulation will reduce the likelihood that the signal conductors will be exposed. The signal wires 612 may be terminated to the electrical contacts 606.

One or more embodiments may include a combination of different features set forth herein. For example, one or more embodiments may have (1) twisted pairs with different twist directions (i.e., some clockwise, others counter-clockwise) and (2) a designated pack ratio of the twisted pairs that permits movement of the twisted pairs relative to one another. Such embodiments may have, for example, at least 32 twisted pairs or more and be configured to communicate analog signals through the twisted pairs at frequencies between 0.5 MHz and 30.0 MHz and have a maximum near end crosstalk that is −26 dB or better. Optionally, the twisted pairs may include "asymmetric twisted pairs" in which the conductors of the twisted pair have different cross-sectional areas (e.g., ground conductor having a greater diameter than the signal conductor).

One or more embodiments may have (1) asymmetric twisted pairs and (2) a designated pack ratio of the twisted pair that permits movement of the wire pairs relative to one another. Such embodiments may have at least 32 twisted pairs or more and be configured to communicate analog signals through the twisted pairs at frequencies between 0.5 MHz and 30.0 MHz and have a maximum near end crosstalk that is −26 dB or better. Optionally, at least some of the twisted pairs may have different twist directions.

Yet in other embodiments, the wire pairs may be parallel-pairs that have a designated braided arrangement of the wire pairs such that the wire pairs are tightly packed but are braided in a manner so that the positions of the wire pairs relative to one another change. Such embodiments may have at least 32 twisted pairs or more and be configured to communicate analog signals through the twisted pairs at frequencies between 0.5 MHz and 30.0 MHz and have a maximum near end crosstalk that is −26 dB or better. Optionally, the wire pairs may include asymmetric wire pairs in which the conductors of the twisted pair have different cross-sectional areas.

Figure 17:
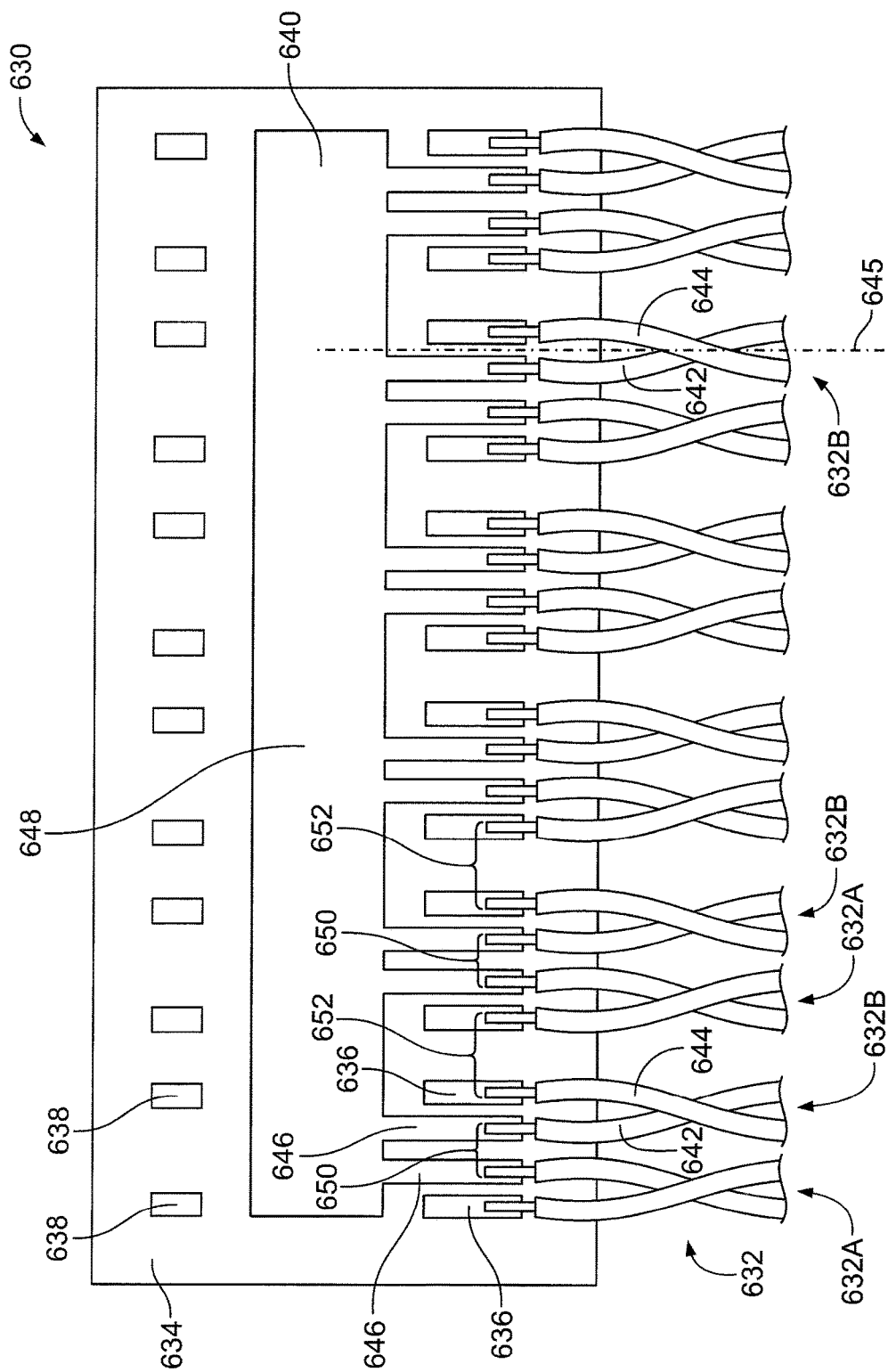
FIG. 17 is a plan view of a sub-assembly that may be used to communicatively couple the wire pairs to other components.

The communication sub-assembly 630 of FIG. 17 is similar to the communication sub-assemblies 500, 600 (FIGS. 15 and 16, respectively). For example, the communication sub-assembly 630 includes a printed circuit 634 and twisted pairs 632 having respective insulated signal wires 642 and insulated ground wires 644. The twisted pairs 632 form a ribbon layer. As shown, some of the twisted pairs 632 are twisted about a respective central axis 645 in a first direction (designated as twisted pairs 632A) and some of the twisted pairs 632 are twisted about the central axis 645 in a different second direction (designated as twisted pairs 632B). The insulated signal wires 642 are configured to be electrically connected to corresponding electrical contacts 636, which are electrically coupled to electrical contacts 638 at an opposite end of the printed circuit 634. The insulated ground wires 644 are configured to be electrically coupled to a ground plane 640 at electrical contacts 646, which are traces extending from a main portion 648 of the ground plane 640. Optionally, the main portion 648 may be embedded within the printed circuit 634.

In some embodiments, at least some of the twisted pairs 632 may be spaced apart from one another at greater distances. For example, each of the twisted pairs 632A is positioned adjacent to an associated twisted pair 632B such that the insulated ground wires 644 are positioned between the insulated signal wires 642. The associated twisted pairs 632A, 632B are separated by a separation distance 650. Other twisted pairs may be separated by a greater distance. For example, the insulated signal wires 642 that are adjacent to one another may be separated by a separation distance 652 that is greater than the separation distance 650.

Figure 18:
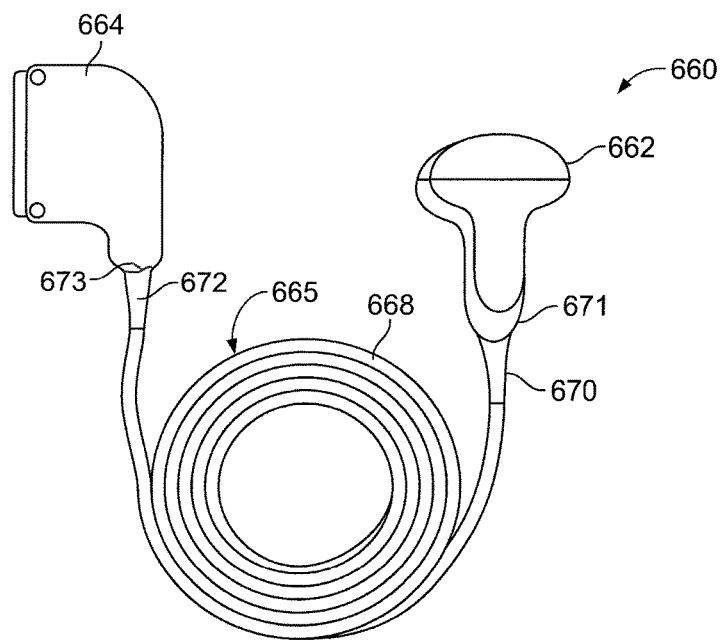
FIG. 18 illustrates a probe assembly formed in accordance with an embodiment.

FIG. 18 illustrates a probe assembly 660 formed in accordance with an embodiment. The probe assembly 660 includes an ultrasound probe or transducer 662, a system connector 664, and a cable assembly 665 that extends between and communicatively couples the ultrasound probe 662 to the system connector 664. The ultrasound probe 662 includes an array 663 of transducer elements (not shown). The transducer elements may be, for example, piezoelectric elements, capacitive micromachined ultrasonic transducer (CMUT) elements, or piezoelectric micromachined ultrasound transducer (PMUT) elements. The transducer elements may be similar to those described with respect to FIGS. 24-27 in U.S. application Ser. No. 14/837,842 ("the '842 Application"). This portion of the '842 Application is incorporated herein by reference. The signal wires are electrically coupled to respective transducer elements.

The system connector 664 is configured to mate with a port of the control system (not shown). The system connector 664 may include, for example, at least one of a multiplexer circuit, a tuning circuit, or a cable termination board. The cable assembly 665 includes a cable jacket 668 that extends between opposite ends 671, 673. The cable jacket 668 (or the cable assembly 665) may include a strain relief 670 that includes the end 671 and a strain relief 672 that includes the end 673.

In the illustrated embodiment, the probe assembly 660 is configured for external procedures (outside of the patient's body) in which the probe is moved along a patient's skin. Non-limiting examples of such procedures include abdominal sonography, transthoracic echocardiography, breast echography or sonography, hepatic sonography, and the like. However, it is contemplated that the probe assembly may be configured to be suitable for internal procedures, such as transesophageal echocardiography (TEE).

Figure 19:
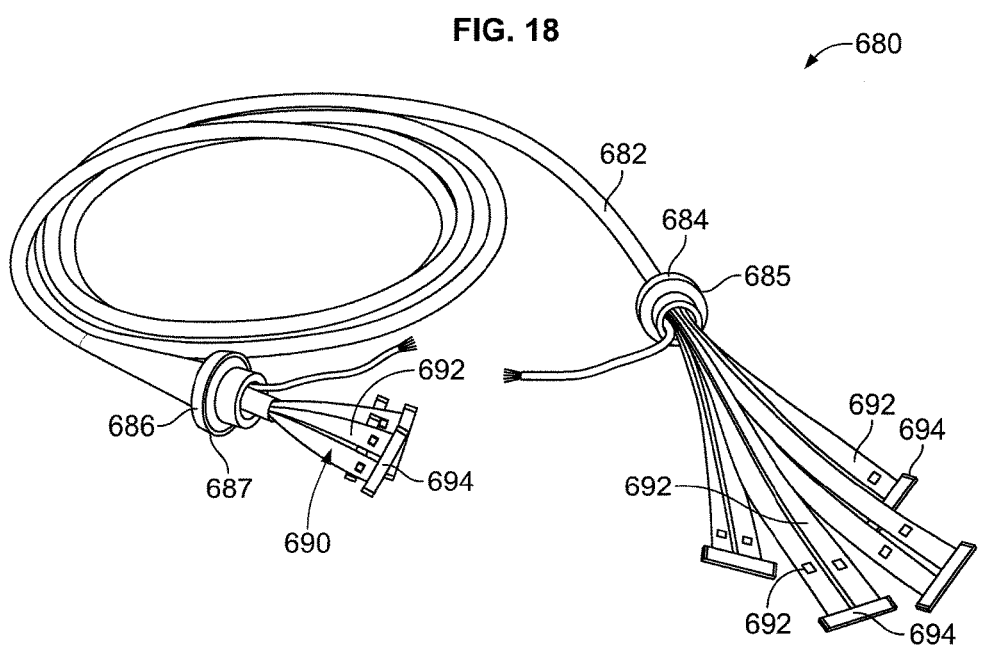
FIG. 19 illustrates a cable assembly formed in accordance with an embodiment.

FIG. 19 illustrates a cable assembly 680 formed in accordance with an embodiment. The cable assembly 680 includes a cable jacket 682 having strain reliefs 684, 686 that include opposite ends 685, 687, respectively, of the cable jacket 682. Also shown, the cable assembly 680 includes twisted pairs 690 that extend beyond (or clear) the ends 685, 687. The twisted pairs 690 are arranged in designated groups 692. The twisted pairs 690 of each of the designated groups 692 are coupled to one another such that the twisted pairs 690 of the designated group 692 have predetermined spatial relationships with respect to one another. The twisted pairs 690 of each of the designated groups 692 coincide with a common plane, but other configurations are possible. Each of the designated groups 690 is terminated to a respective wire connector 694. As shown, each of the wire connectors 694 has two designated groups 690 terminated thereto, but additional groups may be terminated or only one group may be terminated to the wire connector 694 in other embodiments. The wire connectors 694 may include printed circuits, such as the printed circuits 504, 604, and 634.

Figure 20:
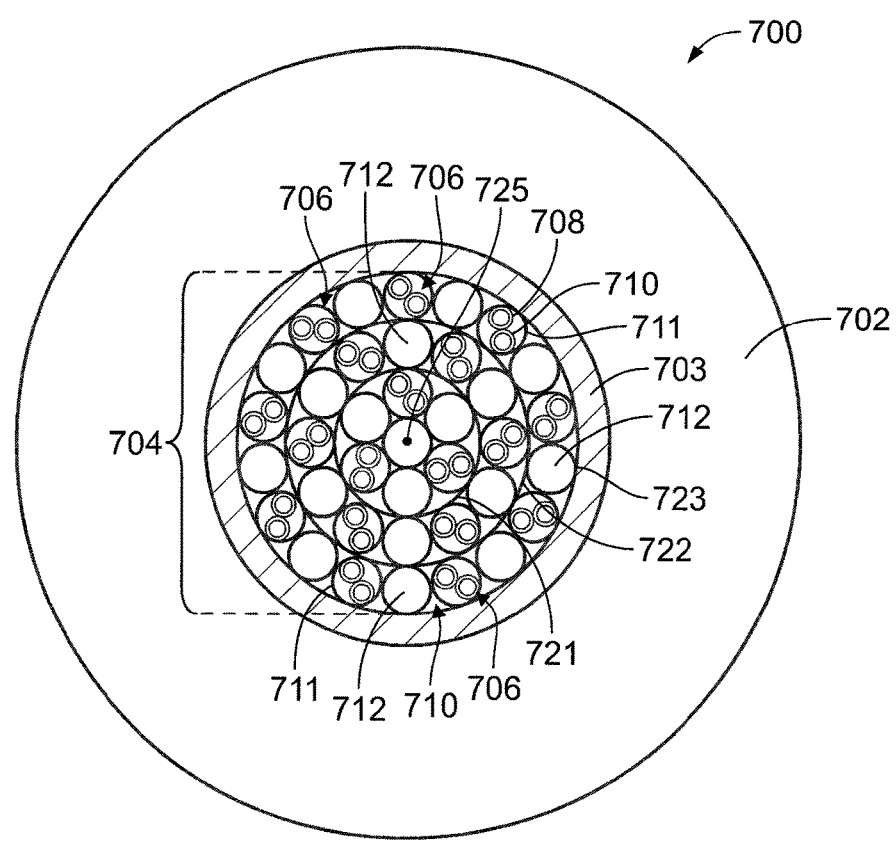
FIG. 20 is a cross-section of a cable assembly having a designated pack ratio formed in accordance with an embodiment.

FIG. 20 is a cross-section of a cable assembly 700 having a designated arrangement of wire pairs in accordance with an embodiment. The cable assembly 700 includes a channel 704 that is surrounded by a shielding layer 703 (e.g., braided shield) and a cable jacket 702. The cable assembly 700 also includes a plurality of wire pairs 706 extending through the channel 704. The wire pairs 706 are twisted pairs. The wire pairs 706 may include an insulated signal wire 708 and an insulated ground wire 710. The wire pairs 706 twist within a substantially circular profile (indicated by 711). Alternatively, the wire pairs 706 may include two insulated signal wires and an optional drain wire configured for differential communication. The channel 704 has a designated size and shape.

The cable assembly 700 also includes longitudinal elements 712, which may also be referred to as spacers. The longitudinal elements 712 extend adjacent to one or more wire pairs 706 through the channel. In particular embodiments, the wire pairs 706 are arranged in levels or valences. For example, the cable assembly 700 includes a first level 721 having three wire pairs 706, a second level 722 having six wire pairs 706, and a third level 723 having nine wire pairs 706. The wire pairs 706 of each level wrap helically around a central axis 725 of the cable assembly 700. Each of the levels also includes a plurality of the longitudinal elements 712 that separate adjacent wire pairs 706.

The cable assembly 700 may have a packed arrangement of wire pairs 706 in which the wire pairs 706 essentially maintain the relative positions with respect to one another in the channel 704. The relative positions are maintained because of a predetermined bunching of the longitudinal elements 712 and the wire pairs 706. The shielding layer 703 and/or the cable jacket 702 may be sized and shaped to tightly hold the longitudinal elements 712 and the wire pairs 706 in the packed arrangement. As shown, each of the wire pairs 706 in the first and second levels 721 and 722 directly contact at least three longitudinal elements 712.

In some embodiments, the wire pairs 706 of one level are helically wrapped about the central axis 725 in first direction (e.g., right-hand or clockwise) and the wire pairs 706 of the adjacent level (or levels) are wrapped about the central axis 725 in a second direction (e.g., left-hand or counter-clockwise). As such, the levels of wire pairs may have different wrap orientations.

Alternatively or in addition to the above, the wire pairs 706 have different twist orientations (e.g., right-hand and left-hand or clockwise and counter-clockwise) about the axis of the wire pair and/or twist at different rates. For example, the wire pairs 706 of a one level may have a twist orientation about the axis of the twisted pair that differs from the wire pairs 706 of an adjacent level or levels. For example, the wire pairs 706 of the first level 721 may have a right-hand twist, the wire pairs 706 of the second level 722 may have a left-hand twist, and the wire pairs 706 of the first level may have a right-hand twist. Optionally, the channel 710 may be filled with a liquid, such as an electrically-lossy material, that exists between the wire pairs 706 and longitudinal elements 712 during operation.

Yet in an alternative embodiment, the wire pairs within a single level have different twist orientations (e.g., alternating twist orientations). In this manner, it may be possible for each wire pair to have a different twist orientation with respect to adjacent wire pairs of the same level and/or with respect to adjacent wire pairs of different levels.

Optionally, the wire pairs, the longitudinal elements, and the channel are configured to have a designated pack ratio ($Area^{WPS}/Area^C$), wherein the $Area^{WPS}$ includes a collective cross-sectional area of the wire pairs and the longitudinal elements and the $Area^C$ is equal to a cross-sectional area of the channel, the channel being the space through which the wire pairs and the other longitudinal elements, if any, are permitted to extend.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The patentable scope should, therefore, be determined with reference to the appended claims, along with the full scope of equivalents to which such claims are entitled.

As used in the description, the phrase "in an exemplary embodiment" and the like means that the described embodiment is just one example. The phrase is not intended to limit the inventive subject matter to that embodiment. Other embodiments of the inventive subject matter may not include the recited feature or structure. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A probe assembly comprising:
    an ultrasound probe; and
    a cable assembly configured to communicatively couple the ultrasound probe to a control system and transmit analog signals therethrough, the cable assembly comprising:
        a cable jacket surrounding a channel of the cable assembly; and
        at least 32 wire pairs extending through the channel, the channel being sized and shaped to permit the wire pairs to move relative to one another within the channel when the probe assembly is moved, the channel being an available space through which the wire pairs and optional longitudinal elements are permitted to extend through during operation of the probe assembly, the wire pairs and the channel being configured to have a designated pack ratio ($Area^{WPS}/Area^{C}$), wherein the $Area^{WPS}$ includes a collective cross-sectional area of the wire pairs and the longitudinal elements extending through the channel, and wherein the $Area^{C}$ is equal to a cross-sectional area of the channel, the designated pack ratio being between 0.20 and 0.75,
    wherein the wire pairs include first twisted pairs and second twisted pairs, each of the first twisted pairs being twisted in a first direction about a central axis of the corresponding first twisted pair, each of the second twisted pairs being twisted in an opposite second direction about a central axis of the corresponding second twisted pair, and
    wherein the twisted pairs form a plurality of ribbon layers in which each of the ribbon layers has at least two of the first twisted pairs and at least two of the second twisted pairs.

2. The probe assembly of claim 1, wherein the first twisted pairs and the second twisted pairs are interspersed within the channel.

3. The probe assembly of claim 1, wherein the first twisted pairs and the second twisted pairs have an alternating arrangement with respect to one another for each ribbon layer, wherein the alternating arrangement includes at least one of: (a) each first twisted pair being adjacent to at least one second twisted pair or (b) each second twisted pair being adjacent to at least one first twisted pair.

4. The probe assembly of claim 1, further comprising a communication sub-assembly having a printed circuit, the first and second twisted pairs being terminated to the printed circuit.

5. The probe assembly of claim 1, wherein the designated pack ratio is between 0.45 and 0.65.

6. The probe assembly of claim 1, wherein the cable assembly further comprising longitudinal elements that extend through the channel, the $Area^{WPS}$ including the collective cross-sectional area of the wire pairs and the collective cross-sectional area of the longitudinal elements.

7. The probe assembly of claim 1, wherein the wire pairs form a plurality of ribbon layers, the wire pairs of each ribbon layer being terminated to a printed circuit.

8. The probe assembly of claim 1, wherein the wire pairs include at least 64 wire pairs.

9. The probe assembly of claim 1, wherein the probe assembly is configured to communicate the analog signals through the wire pairs at frequencies between 0.5 MHz and 50.0 MHz and have a maximum near end crosstalk that is −26 dB or better.

10. A probe assembly comprising:
    an ultrasound probe; and
    a cable assembly configured to communicatively couple the ultrasound probe to a control system and transmit analog signals therethrough, the cable assembly comprising:
        a cable jacket surrounding a channel of the cable assembly; and
        at least 32 wire pairs extending through the channel, the channel being sized and shaped to permit the wire pairs to move relative to one another within the channel when the probe assembly is moved, the channel being an available space through which the wire pairs and optional longitudinal elements are permitted to extend through during operation of the probe assembly, the wire pairs and the channel being configured to have a designated pack ratio ($Area^{WPS}/Area^{C}$), wherein the $Area^{WPS}$ includes a collective cross-sectional area of the wire pairs and the longitudinal elements extending through the channel, and wherein the $Area^{C}$ is equal to a cross-sectional area of the channel, the designated pack ratio being between 0.20 and 0.75,
    wherein each of the wire pairs includes an insulated ground wire having a wire conductor and an insulation layer and also includes an insulated signal wire having a wire conductor and an insulation layer, the wire conductor of the insulated ground wire having a first cross-sectional area and the wire conductor of the insulated signal wire having a second cross-sectional area, the first cross-sectional area being greater than the second cross-sectional area.

11. The probe assembly of claim 10, wherein the wire pairs include first twisted pairs and second twisted pairs, each of the first twisted pairs being twisted in a first direction about a central axis of the corresponding first twisted pair, each of the second twisted pairs being twisted in an opposite second direction about a central axis of the corresponding second twisted pair.

12. A cable assembly comprising:
    a cable jacket surrounding a channel of the cable assembly, the cable jacket extending between opposite ends; and
    at least 32 wire pairs extending through the channel, the channel being sized and shaped to permit the wire pairs to move relative to one another within the channel when the probe assembly is moved, the channel being an available space through which the wire pairs and optional longitudinal elements are permitted to extend through the cable jacket during usage of the cable assembly, wherein the wire pairs and the channel are configured to have a designated pack ratio (Area$^{WPS}$/Area$^C$), wherein the Area$^{WPS}$ includes a collective cross-sectional area of the wire pairs and the longitudinal elements extending through the channel, and wherein the Area$^C$ is equal to a cross-sectional area of the channel, the designated pack ratio being between 0.20 and 0.75, wherein each of the wire pairs includes an insulated ground wire having a wire conductor and an insulation layer and also includes an insulated signal wire having a wire conductor and an insulation layer, the wire conductor of the insulated ground wire having a first cross-sectional area and the wire conductor of the insulated signal wire having a second cross-sectional area, the first cross-sectional area being greater than the second cross-sectional area.

13. The cable assembly of claim 12, wherein the wire pairs include first twisted pairs and second twisted pairs, each of the first twisted pairs being twisted in a first direction about a central axis of the corresponding first twisted pair, each of the second twisted pairs being twisted in an opposite second direction about a central axis of the corresponding second twisted pair.

14. The cable assembly of claim 13, wherein the first twisted pairs and the second twisted pairs are interspersed within the channel.

15. The cable assembly of claim 12, wherein the designated pack ratio is between 0.45 and 0.65.

16. The cable assembly of claim 12, further comprising a communication sub-assembly having a printed circuit, the wire pairs being terminated to the printed circuit.

17. A cable assembly comprising:
a cable jacket surrounding a channel of the cable assembly, the cable jacket extending between opposite ends; and
at least 32 twisted pairs extending through the channel that each include an insulated signal wire and an insulated ground wire, the twisted pairs including first twisted pairs and second twisted pairs, the first twisted pairs being twisted in a first direction, the second twisted pairs being twisted in an opposite second direction.

18. A probe assembly comprising:
a cable assembly comprising:
a cable jacket surrounding a channel of the cable assembly, the cable jacket extending between opposite ends; and
at least 32 twisted pairs extending through the channel that each include an insulated signal wire and an insulated ground wire, the twisted pairs including first twisted pairs and second twisted pairs, the first twisted pairs being twisted in a first direction, the second twisted pairs being twisted in an opposite second direction; and
an ultrasound probe, the cable assembly configured to communicatively couple the ultrasound probe to a control system and transmit signals therethrough.

* * * * *